(12) United States Patent
Hill, Jr. et al.

(10) Patent No.: US 11,726,102 B2
(45) Date of Patent: Aug. 15, 2023

(54) PARTICLE-BASED DRUG DETECTION METHOD AND DEVICE EMBODIMENTS

(71) Applicants: Herbert H. Hill, Jr., Pullman, WA (US); Brian Clowers, Pullman, WA (US); Nicholas Lovrich, Pullman, WA (US)

(72) Inventors: Herbert H. Hill, Jr., Pullman, WA (US); Brian Clowers, Pullman, WA (US); Nicholas Lovrich, Pullman, WA (US)

(73) Assignee: Washington State University, Pullman, WA (US)

( * ) Notice: Subject to any disclaimer, the term of this patent is extended or adjusted under 35 U.S.C. 154(b) by 1273 days.

(21) Appl. No.: 16/227,554

(22) Filed: Dec. 20, 2018

(65) Prior Publication Data

US 2019/0195899 A1    Jun. 27, 2019

Related U.S. Application Data

(63) Continuation-in-part of application No. 15/217,856, filed on Jul. 22, 2016, now abandoned.
(Continued)

(51) Int. Cl.
*G01N 33/94* (2006.01)
*G01N 33/497* (2006.01)
(Continued)

(52) U.S. Cl.
CPC ....... *G01N 33/948* (2013.01); *A61B 10/0051* (2013.01); *G01N 1/2214* (2013.01); *G01N 1/405* (2013.01); *G01N 1/4022* (2013.01); *G01N 1/44* (2013.01); *G01N 33/483* (2013.01); *G01N 33/487* (2013.01); *G01N 33/4833* (2013.01);
(Continued)

(58) Field of Classification Search
CPC .... G01N 1/405; G01N 1/4022; G01N 1/2214; G01N 1/44; G01N 33/48; G01N 33/483; G01N 33/4833; G01N 33/497; G01N 33/487; G01N 33/948; G01N 2033/4975; G01N 27/624; G01N 2001/2244; G01N 2001/028; G01N 2001/022; A61B 10/0051; A61B 5/082; A61B 2010/0009;
(Continued)

(56) References Cited

U.S. PATENT DOCUMENTS 4,988,628 A * 1/1991 Nanji ............... G01N 33/94 436/178
5,065,614 A * 11/1991 Hartman ............ G01N 1/405 73/23.35
(Continued)

OTHER PUBLICATIONS

Nanji et al. Clinical Toxicology, vol. 25(6), pp. 501-515, 1987.*
(Continued)

*Primary Examiner* — Maureen Wallenhorst
(74) *Attorney, Agent, or Firm* — Klarquist Sparkman, LLP

(57) ABSTRACT

Disclosed herein are embodiments of methods for detecting the presence of and amount of drugs in a sample, particularly a particle sample obtained from a subject. In particular disclosed embodiments, the particle samples are skin particle samples, saliva particle samples, and/or mucous samples isolated from a subject and analyzed using thermal desorption methods combined with a selected detection method.

17 Claims, 12 Drawing Sheets

Related U.S. Application Data

(60) Provisional application No. 62/196,440, filed on Jul. 24, 2015.

(51) Int. Cl.

| | | |
|---|---|---|
| *G01N 33/487* | (2006.01) | |
| *G01N 1/40* | (2006.01) | |
| *G01N 1/22* | (2006.01) | |
| *G01N 1/44* | (2006.01) | |
| *G01N 33/483* | (2006.01) | |
| *A61B 10/00* | (2006.01) | |
| *G01N 1/02* | (2006.01) | |

(52) U.S. Cl.
CPC .... *G01N 33/497* (2013.01); *A61B 2010/0009* (2013.01); *G01N 2001/022* (2013.01); *G01N 2001/028* (2013.01); *G01N 2001/2244* (2013.01); *G01N 2033/4975* (2013.01)

(58) Field of Classification Search
CPC ......... Y10T 436/142222; Y10T 436/24; Y10T 436/25; Y10T 436/25375; Y10T 436/25875
USPC ... 436/63, 93, 147, 161, 164, 165, 173, 174, 436/177, 181; 422/70, 82.05, 83, 84, 85, 422/86, 89, 530
See application file for complete search history.

(56) References Cited

U.S. PATENT DOCUMENTS

| | | | |
|---|---|---|---|
| 6,378,385 B1 | 4/2002 | Bowers | |
| 7,465,586 B2* | 12/2008 | Day | G01N 33/948 |
| | | | 436/63 |
| 9,976,944 B2 | 5/2018 | Olin et al. | |
| 10,520,439 B2* | 12/2019 | Palmskog | A61B 5/412 |
| 2004/0114130 A1* | 6/2004 | Nguyen | G01N 1/24 |
| | | | 356/36 |
| 2008/0128609 A1 | 7/2008 | Miller et al. | |
| 2009/0017555 A1 | 1/2009 | Jehanli et al. | |
| 2009/0024060 A1 | 1/2009 | Darrigrand et al. | |
| 2010/0116021 A1 | 5/2010 | O'Brien | |
| 2010/0297635 A1 | 11/2010 | Olin et al. | |
| 2011/0127421 A1 | 6/2011 | Finlay | |
| 2012/0049055 A1 | 3/2012 | Hashimoto et al. | |
| 2012/0329168 A1* | 12/2012 | Lin | G01N 21/783 |
| | | | 422/86 |
| 2013/0157381 A1 | 6/2013 | Pang et al. | |
| 2014/0288454 A1 | 9/2014 | Paz et al. | |
| 2014/0331744 A1* | 11/2014 | Van Egmond | H05B 6/36 |
| | | | 29/606 |
| 2015/0025407 A1 | 1/2015 | Eichler et al. | |
| 2015/0305651 A1 | 10/2015 | Attariwala et al. | |
| 2015/0346170 A1 | 12/2015 | Huang et al. | |

OTHER PUBLICATIONS

Sonnberg et al. Analytical and Bioanalytical Chemistry, vol. 407, pp. 5999-6008, Jun. 14, 2015.*
Lawrence, A.H. Forensic Science International, vol. 34, pp. 73-83, 1987.*
Lawrence et al. Journal of Clinical Laboratory Analysis, vol. 2, pp. 101-107, 1988.*
Gentili et al. Journal of Chromatography B, vol. 801, pp. 289-296, 2004.*
Karasek et al. "Detection of lysergic acid diethylamide, delta-9-tetrahydrocannabinol and related compounds by plasma chromatography." *J Chromatogr.*, 105(2): 345-352, Feb. 26, 1975.
Lee et al. "Oral Fluid-Plasma Cannabinoid Ratios Following Controlled Oral THC and Smoked Cannabis Administration." *Anal Bioanal Chem.*, 405(23): 7269-7279, Jul. 6, 2013.

* cited by examiner

PARTICLE-BASED DRUG DETECTION METHOD AND DEVICE EMBODIMENTS

CROSS REFERENCE TO RELATED APPLICATION

This application is a continuation-in-part of U.S. patent application Ser. No. 15/217,856, filed on Jul. 22, 2016, now abandoned, which in turn claims the benefit of and priority to the earlier filing date of U.S. Provisional Patent Application No. 62/196,440, filed on Jul. 24, 2015; the entirety of each of these prior applications is incorporated by reference herein.

FIELD

The present disclosure concerns embodiments of methods for detecting $\Delta^9$-tetrahydrocannabinol (THC), other drugs, or metabolites thereof using particle samples obtained from subjects.

BACKGROUND

With the spread of legalization of marijuana there is a growing need for detection methods and devices that can be used by law enforcement to aid in identifying people driving under the influence of marijuana, as well as by employers in the public and private sectors. $\Delta^9$-Tetrahydrocannabinol (THC) is the main psychoactive cannabinoid in marijuana. Due to the type of media typically isolated for drug testing, such as urine and/or blood, drug analysis typically requires specialty training to collect and handle samples, particularly due to biological hazard issues. Also, conventional testing methods typically require extensive time periods to collect and analyze such samples, thereby rendering such tests invasive and impractical for on-the-spot testing.

Currently, the only widely used method for on-site detection of cannabis is a lengthy series of 12 psychological and physical tests that are performed to evaluate the drug intoxication level of a suspect. In law enforcement, specially trained law enforcement officers called "drug recognition experts" or Advanced Roadside Impaired Driving Enforcement officers administer these tests to suspected drugged drivers to classify the type(s) of drugs causing the impairment. The classification can then be confirmed by blood analysis from the state toxicology laboratory. Conventional methods for drug analysis in the workplace typically rely on urine analysis, which is invasive, expensive, and not time efficient.

There exists a need in the art for reliable, fast, and non-invasive methods of detecting THC in subjects that can be used by authorities in the field and/or in the workplace. Such a rapid, on-site test for the identification of THC (or related compounds) from a human sample would aid authorities in identifying intoxicated individuals and determine when to request a warrant for a blood test and also would aid employers when testing for workplace compliance. Quick and reliable testing methods also are needed in the health fields to identify whether secondary drug effects (e.g., second-hand smoke; unintended ingestion, or the like) have compromised the health of a subject.

SUMMARY

Disclosed herein are embodiments of methods comprising obtaining a particle sample from a subject, exposing the particle sample to heat using thermal desorption to produce a volatilized sample from the particle sample, and analyzing the volatilized sample to determine the presence of THC or other semi-volatile drugs in the particle sample using spectrometry detection techniques, visual detection techniques, chromatography detection techniques, or combinations thereof. In particular disclosed embodiments, the particle sample is a skin particle sample, a saliva particle sample, or a mucous particle sample.

In additional embodiments, the methods can comprise obtaining a particle sample from a subject using a breathalyzer device capable of collecting a breath sample from the subject, exposing the particle sample to heat using thermal desorption to produce a volatilized sample from the particle sample, and analyzing the volatilized sample with the breathalyzer device to determine the presence of THC in the particle sample by viewing a THC signature peak, a color change, or a read-out message produced by such a THC signature peak and/or color change, or a combination thereof, using the breathalyzer device.

In yet additional embodiments, the methods can comprise obtaining a particle sample from a subject using a swab capable of collecting the particle sample from the subject, placing the swab into a detection device, exposing the swab comprising the particle sample to heat using thermal desorption to produce a volatilized sample from the particle sample, analyzing the volatilized sample with the detection device to determine the presence of one or more signature peaks and/or color changes, or a corresponding read-out representing a signature peak and/or color change, provided by the detection device.

The foregoing and other objects, features, and advantages of the present disclosure will become more apparent from the following detailed description, which proceeds with reference to the accompanying figures.

DETAILED DESCRIPTION

I. Overview of Terms

Figure 1:
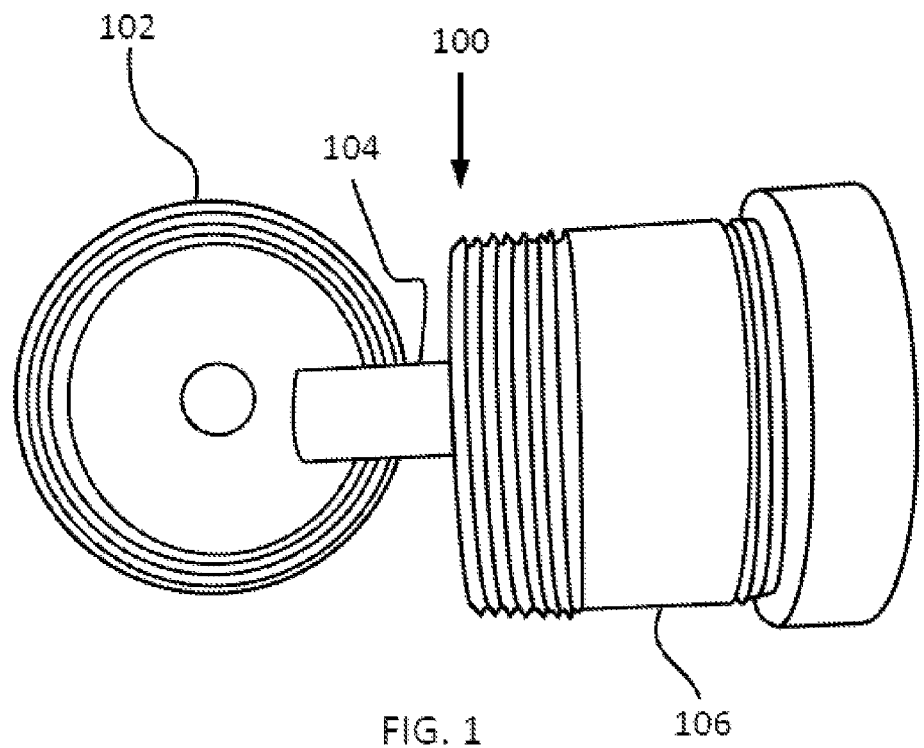
FIG. 1 is a photographic image of a breath collector device used to obtain and isolate particle samples from a subject, wherein the particles may comprise one or more drugs or metabolites thereof.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided.

Collection Device: A device by which particles, particularly skin particles are isolated from a subject, which can include a breathalyzer device as described herein; a particle-trapping component of such a device; a swab or other adsorbent component; or a combination thereof.

Mucous Particle Samples: These types of particles include mucous that comprises skin or hair particles.

Particle Sample: A sample obtained from a subject that is analyzed using methods described herein to determine whether semi-volatile drugs are adsorbed onto the particle sample. Particle samples include skin particle samples, saliva particles samples, and mucous particle samples.

Saliva Particle Samples: These types of particles comprise saliva, which in particular embodiments, further comprises skin particles.

Semi-Volatile: This term refers to a property of a drug and indicates that the drug is not volatile at certain temperatures. In some embodiments, the drug may not be volatile at temperatures below 100° C., such as greater than 25° C. to 99° C., or greater than 25° C. to 90° C., or 50° C. to 85° C., or that the drug has a vapor pressure ranging from greater than 0 torr to less than 10 torr at body temperatures ranging from 35° C. to 41° C., such as 35° C. to 40° C., or 36° C. to 38° C., or 37° C.

Subject: A human or non-human animal.

THC Signature Peak: A peak that is obtained using a spectrometry or chromatography detection method described herein. Exemplary signature peaks are described herein, but others are contemplated.

Thermal Desorption: A process by which a drug that has been adsorbed onto or otherwise is associated with a particle sample and/or a collection device described herein is exposed to a heat source that provides a temperature capable of volatilizing the drugs so as to desorb them from the particles to which they are adsorbed. In some embodiments, thermal desorption can further comprise using carrier gas to facilitate transport of the volatilized drugs to a detection system. Thermal desorption can involve heating with or without inductive heating.

Volatilized Sample: A vapor-state sample produced by exposing the particle samples disclosed herein to heat, such as by using thermal desorption, so as to volatilize drugs adsorbed onto or otherwise is associated with a particle sample and/or a collection device described herein into a vapor state for further analysis.

II. Introduction

Alcohol breathalyzer tests are used by law enforcement to aid in the identification of drunk drivers and this method has been accepted by the general public for this use for decades. There is still a need, however, for methods and field-friendly devices for detecting THC and semi-volatile drugs that cannot be detected by methods used for alcohol analysis/detection. Such methods and devices would be of great value not only in determining whether individuals are under the influence of such drugs when driving, but also for determining compliance with workplace requirements and/or other areas in which drug detection is needed, such as in the medical and/or veterinary fields.

THC and other semi-volatile drugs are not as volatile as ethanol and thus cannot be collected or detected in the same manner as ethanol. Typically, THC and other semi-volatile drugs have low vapor pressures. For example, THC has a vapor pressure of $4.6 \times 10^{-8}$ mmHg at 25° C. Since these drugs are not volatile compounds like ethanol, it is challenging to introduce them into an analysis system, and even if they are successfully introduced, they often are introduced at very low concentrations, which makes detection difficult. These drawbacks are prevalent problems with breath samples. Currently breath analysis has focused on capturing the volatile compounds from breath.

To date, methods for detecting intoxication due to drugs, particularly THC, rely on analyzing THC vapor directly isolated from a subject's breath, not THC particles or particle samples comprising THC. Other conventional methods for determining the presence of drugs, such as THC, require analysis of blood, urine, or hair samples, which necessitates laboratory-level analytical techniques and longer analysis time periods (e.g., on the order of months). These sample mediums have very long windows of detection, therefore with the current analysis methods they will give a positive detection beyond the time the psychoactive effects are being experienced.

With reference to THC as an exemplary drug, the psychoactive effects of the drug are generally felt within minutes after being consumed, but it can take at least 20 minutes for the concentration in the body to build up to intoxication levels. The time frame to reach mandated intoxication levels for cannabis can vary depending on how much was used, how it was used, body mass index of the user, and history of prior use. It has been estimated that the psychoactive effects of THC after inhalation are felt 2 to 4 hours after initial consumption. Blood analyses by GC-MS or LC-MS are the main conformational tests for identifying drugged subjects. THC can only be detected in the blood for 3.5 to 5.5 hours after inhalation, but due to delayed sample collection THC cannot always be identified in the blood samples collected from a subject. THC metabolites, THC-COOH and 11-OH-THC, also can be used to confirm cannabis abuse from blood samples, but THC and its metabolites can be detected in human samples 1.3 days (occasional users) up to 15 days (chronic users) after use, long after the psychoactive effects have passed. The amount of THC in the cannabis consumed also influences the timeframe that THC and THC metabolites can be detected in blood samples. As the time frame for conventional methods of detecting THC extends well beyond the intoxication time period, identifying cannabis intoxication by THC metabolites and/or using conventional detection techniques are not reliable methods for field use, where it is important to identify if the subject is intoxicated at the time the sample is obtained.

Blood and urine samples are not applicable for on-site collection. Conventional analysis methods for used to analyze these samples, such as gas chromatography (GC-MS) and liquid chromatography (LC-MS), are not field-portable. Consequently, blood, urine, and hair are not sample mediums that are appropriate for on-site testing of subjects. Additionally, positive detection of THC from sweat does not always indicate the consumption of cannabis. For THC to be detectable by sweat samples, a high amount of sweat is needed, typically over 5 mL. Such a requirement leads to false negatives—that is, the inability to detect the presence of the drug if less than 5 mL of sweat is collected. Another drawback of this type of sample is the fact that the time window for detecting THC from sweat samples is too narrow; it does not cover the estimated 4-hour time frame of the psychoactive effects of THC. Oral fluid samples also have the drawback of providing too many false negatives to be a functional field detection method to aid law enforcement in detecting drugged drivers.

Without being limited to a particular theory, it is currently believed that THC and other semi-volatile drugs can be adsorbed onto skin in a subject's mouth, as well as other areas of the respiratory system. Skin particles are continuously removed naturally from subjects, and if the subject has smoked or otherwise ingested THC or other semi-volatile drugs, such drugs will be adsorbed to the skin particles. For example, when cannabis is smoked or otherwise ingested, the first thing that THC comes into contact with is the skin coating the inside of the mouth, throat, and lungs (when inhaled). Particles comprising THC may be expelled from a subject while breathing and thus can be collected by isolating these breathed particles and/or these particles can be collected via a simple swab of the nose, tongue, or cheek.

Disclosed herein are embodiments of methods that utilize particle samples as a medium for determining the presence of semi-volatile drugs in a sample. Thus, at least one inventive aspect of the disclosed methods involves determining the presence of THC and other drugs, or metabolites thereof. In exemplary embodiments, the disclosed methods can be used to detect and quantify the presence of drugs, such as cannabindiol, cannabinol, morphine, cocaine, methamphetamine hydrochloride, dextromethorphan hydrobromide, or the like, on physical particle samples by specifically isolating the particles from a subject and analyzing these particle samples. In contrast, conventional methods physically remove any such particles from the breath of a subject without any analysis of these particles. Instead, the particles are discarded and the analysis proceeds with analyzing the exhaled breath flow. As such, conventional methods separate and remove the particle samples that are used in the presently disclosed methods.

The disclosed method and device embodiments of the present disclosure allow for the detection of analytes of interest in samples without residual identifying components remaining in the sample, such as nucleic acid components (e.g., DNA, RNA, or fragments thereof). The disclosed method and device embodiments provide the additional ability to render any such nucleic acid components undetectable, thereby eliminating any legal and/or privacy concerns associated with isolating the samples. In some embodiments, the nucleic acid component can be rendered undetectable by exposing the sample to a suitable temperature, such as a temperature at or within the temperature ranges disclosed herein. In yet additional embodiments, the nucleic acid component can be rendered undetectable by chemically or biologically destroying the nucleic acid component.

III. Methods

Disclosed herein are embodiments of methods used to determine the presence of and/or amount of drugs in a particle sample. In particular disclosed embodiments, the methods are directed to measuring the presence and/or amount of THC and/or other semi-volatile drugs adsorbed onto particle samples using detection techniques suitable for analyzing such samples in a fast and reliable manner. The methods disclosed herein comprise isolating and analyzing particle samples, such as skin particles, saliva particles, and/or mucous particles, to determine the presence of and/or amount of THC (or other semi-volatile drugs) in the particle samples. As such, the methods disclosed herein can be used to determine whether a subject has inhaled or ingested and/or is under the psychoactive influence of such drugs. The disclosed methods use non-invasive isolation techniques to obtain the particle samples. By analyzing particle samples that are non-invasively obtained from a subject, it is possible to identify any drugs present within the sample after such drugs have been used by the subject without. The detection methods described herein provide the added benefit of destroying the biological sample after it has been collected, thus eliminating the need to store biological specimens from subjects. The methods disclosed herein are field-friendly and provide the ability to field-test subjects quickly and easily without the need for benchtop analytical devices or laboratory analytical procedures, which often are required for conventional detection methods.

Embodiments of the methods described herein can comprise obtaining a particle sample from a subject, exposing the particle sample to heat using thermal desorption to produce a volatilized sample from the particle sample, and analyzing the volatilized sample to determine the presence of THC or other semi-volatile drugs in the particle sample using a suitable detection technique.

In particular disclosed embodiments, the methods comprise obtaining the particle sample by isolating a breath sample or swab sample from a subject wherein the breath sample or swab sample comprises the particle sample. As such, isolating and using the actual physical particles (e.g., solid skin particles, liquid saliva particles, and/or solid/liquid mucous particles) obtained from the subject is a particular feature of the disclosed methods—that is, these particles are not simply separated from a subject's breath and then discarded, as is the case with conventional methods. In particular disclosed embodiments, obtaining the particle sample can comprise isolating breath from a subject, wherein the breath sample comprises skin particles. In yet additional embodiments, obtaining the particle sample can comprise swabbing the subject's mouth (or tongue, cheek, or gums) or nose with a swab to collect the particle sample.

In particular disclosed embodiments, the particle sample is a skin particle sample, a saliva particle sample, or a mucous particle sample. In some embodiments, the particle sample is obtained from a subject's mouth, tongue, or nose. Particle samples isolated from a subject's mouth can include particles that are located in the subject's mouth and/or particle samples that are expelled from the subject's lungs to by way of the subject's mouth. Particle samples used in the disclosed methods can be solid particles and/or liquid samples comprising such solid particles. In embodiments where the particle sample is a solid particle, the particles can have sizes ranging from 0.1 μm to 10 μm, such as 0.3 μm to 5 μm, or 0.3 μm to 1 μm.

Some embodiments of the disclosed methods comprise using a breathalyzer device to isolate the breath sample, which can comprise skin particles, saliva particles, or both. In embodiments wherein the method comprises isolating a breath sample from the subject, the subject is allowed to breath into a breathalyzer device for a sufficient amount of time to allow the breathalyzer device to collect at least one particle sample and typically a plurality of particle samples. In particular disclosed embodiments, the breath sample is collected over a time period ranging from 15 seconds to 300 seconds, such as 30 seconds to 120 seconds, or 30 seconds to 60 seconds. In exemplary embodiments, the breath sample (or multiple breath samples) are collected over a time period of at least 1 minute.

Some embodiments of the disclosed methods comprise using a swab to isolate the particle sample, such as saliva particles, mucous particles, or both. Swabs that can be used in the disclosed methods include swabs comprising porous materials, absorbent materials, and/or adsorbent materials. In particular embodiments, the swab comprises a material having a porosity sufficient to adsorb particles having the particle sizes described herein. Exemplary swabs include, but are not limited to, cotton-tipped swabs, rayon-tipped swabs, polytetrafluoroethylene-tipped swabs, polyethylene terephthalate-tipped swabs, polyester-tipped swabs, and metal-containing swabs. In embodiments where the swab is a metal-containing swab, the swab can comprise a metal component embedded within the swab. Suitable metals include, but are not limited to, iron, stainless steel, brass, platinum, gold, combinations or alloys thereof, or other such metals. Such swabs can be useful for embodiments where analysis of the sample involves inductively-coupled heating techniques, which are described herein.

In some embodiments, the methods can further comprise dislodging a particle sample from a subject by exposing the subject to a pulse of air or liquid. The pulse of air or liquid can be applied using a suitable pulsation mechanism, such as a liquid misting device, an air pump device, or other such device. In some embodiments, the methods can comprise pulsating air or liquid into the subject's mouth or nose or onto the subject's tongue. The pulsated air or liquid is projected into the sample's mouth or nose, or on onto the subject's tongue with a force sufficient to cause particle samples to be freed from locations within the subject's mouth (such as locations on the subject's cheeks, teeth, or tongue) or nose. The freed particle samples are then collected by having the subject breath into a breathalyzer device and/or by swabbing areas of the subject's mouth, tongue, or nose. Also, the person may be asked to cough to dislodge particles.

Figure 2:
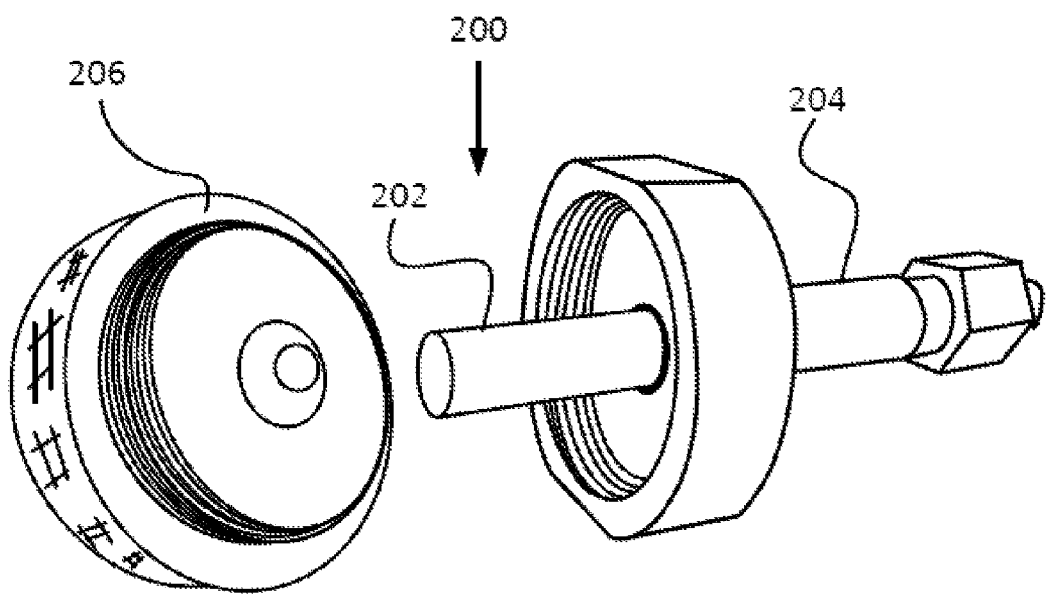
FIG. 2 is a photographic image of a representative thermal desorber component and a particle-trapping component of a device used to isolate particle samples from a subject and thermally desorb a drug from the particle samples.
Figure 16:
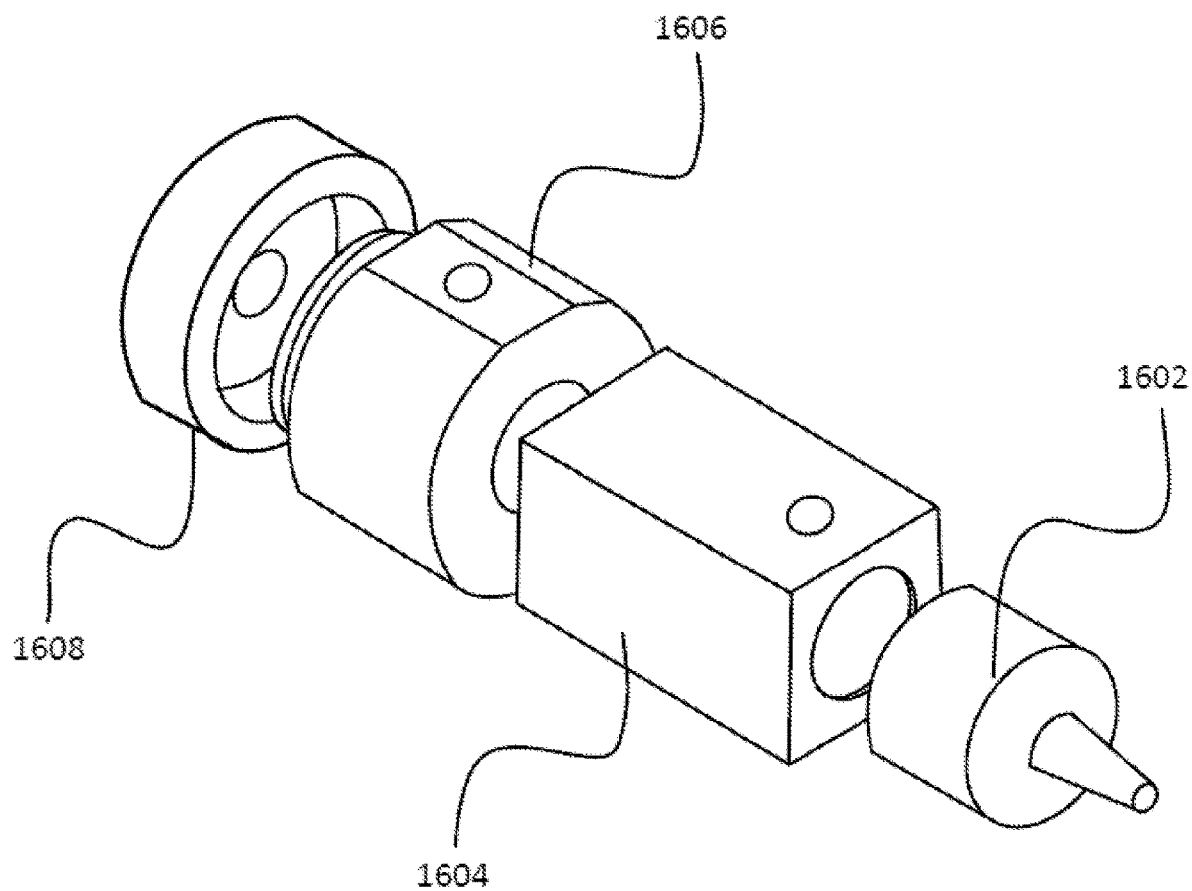
FIG. 16 illustrates an exemplary breathalyzer device that can be used with the disclosed methods.

The methods disclosed herein also comprise exposing the particle sample to heat to desorb any THC, other drugs, or metabolites thereof embedded in the particle sample and/or located on the particle surface. In particular disclosed embodiments, exposing the particle sample to heat can comprise exposing the particle sample to a heat source. The heat source can be any heat source capable of providing temperatures ranging from 100° C. to 500° C., such as 120° C. to 300° C., or 250° C. to 300° C. In particular disclosed embodiments, the heat source is a thermal desorber that can be coupled to a device used to detect the presence of THC, other drugs, or metabolites thereof, such as devices capable of carrying out the detection methods described herein. In some embodiments, the thermal desorber can be coupled to a breath collector device. A representative breath collector device is shown in FIG. 1. With reference to FIG. 1, device 100 comprises a cap 102, a sample conduit through which the sample can be introduced into the device, such as breath mouthpiece 104, and a body 106 that houses the particle trapping component, which is configured to house a collecting medium (not illustrated). Another device 1600 is shown in FIG. 16, which includes a breath mouthpiece component 1602, a drug standard section 1604, a solid phase extraction absorbent chamber 1606, and a backing 1608. These components are interchangeable and therefore can be exchanged, or certain sections can be omitted. The components of a representative thermal desorber are shown in FIG. 2. With reference to FIG. 2, the thermal desorber 200 comprises a particle-trapping component 202 configured to house a collecting medium (not illustrated), a thermal desorber body 204, and a thermal desorber heat source 206. In yet additional embodiments, the particle sample can be exposed to a device capable of desorbing THC, other drugs, or metabolites thereof from the particle sample by way of inductively coupled desorption. In some embodiments, an inductively coupled desorber can comprise a battery or source of electrical current that is passed through a wire coil. When the material to be desorbed is placed inside the coiled wire, the material is heated by induction such that the sample is vaporized into the detector.

The presence of THC, other drugs, or metabolites thereof can be determined using a suitable detection method in combination with thermal desorption. Suitable detection methods include, but are not limited to, visual detection techniques, spectrometry detection techniques (e.g., ion mobility spectrometry, differential mobility spectrometry, photospectrometry, mass spectrometry, or combinations thereof), chromatography detection techniques, or any combination thereof. In particular disclosed embodiments, the detection method is a mobility spectrometry detection technique, such as ion mobility spectrometry (IMS) and/or differential mobility spectrometry (DMS). In some embodiments, the mobility spectrometry technique can be coupled with mass spectrometry. In particular disclosed embodiments, IMS and DMS techniques comprise using an instrument comprising an ionization source, an analyzer, and a detector. IMS and DMS detection techniques can be coupled with chromatographic techniques described herein.

Ion mobility spectrometry, or IMS, is a technique that separates gas phase ions based on the ions' mobility in a carrier gas, with the mobility depending, at least in part, on the ion's mass, charge, size, and shape. IMS techniques typically involve using a drift tube through which the ions travel to a detector. The area of an ion that gas molecules from the carrier gas contact corresponds to the ion's collision cross-section, which is related to the ion size and shape. The greater the collision cross-section (or the larger the ion size), the more area available for the carrier gas to contact and impede the ion's drift through the drift tube. As such, larger ions exhibit longer times to migrate through the drift tube as compared to smaller ions.

Differential mobility spectrometry, or DMS, separates gas phase ions based on differences in chemical structures. In some embodiments, the separation can occur at atmospheric (or ambient) pressure and involves sweeping ions through a DMS cell using a carrier gas (e.g., $N_2$). In some embodiments, a DMS cell can comprise two planar electrodes that are oriented opposite one another so as to provide a space through which a high-voltage radio frequency asymmetric waveform can be applied. A separation voltage is created that causes the ions to oscillate towards one of the two electrodes depending on the difference in the ion's mobility during the high-/low-field portions of the applied waveform. In some embodiments, a direct current voltage can be applied to deflect ions away from the electrodes and towards an associated mass spectrometer for detection.

In method embodiments comprising using IMS and/or DMS detection techniques, a volatilized sample obtained from thermally desorbing the particle samples is exposed to an ionization source of the IMS and/or DMS device component, resulting in an ionized sample. The ionized sample is then allowed to pass through an analyzer component (e.g., an IMS drift tube or a DMS cell) to a detector component. A spectrum can be produced from the information gathered by the detector component that provides different peaks (e.g., signature peaks) corresponding to different components of the volatilized sample. In some embodiments, signature peaks of the sample spectrum include mass peaks that represent particular fragments of a drug compound, or metabolite thereof, or peaks that represent the presence of a drug compound, or metabolite thereof, based on the amount of time needed for it to elute through a column. These signature peaks can be compared to signature peaks of a reference spectrum (that is, a spectrum obtained from applying a similar detection technique to a sample known to contain the drug or drugs of interest). If one or more signature peaks from the sample spectrum matches, or substantially matches the signature peaks of the reference spectrum, the presence of the drug can be confirmed. In particular disclosed embodiments, a THC signature peak can be detected. A THC signature peak can have an associated $K_0$ value of approximately $1.06 \pm 0.02$ $cm^2V^{-1}s^{-1}$. In some embodiments, the THC signature peak can have an associated elution time of approximately 40 seconds to 60 seconds, such as 40 seconds to 55 seconds, or 40 seconds to 50 seconds, or 40 seconds to 45 seconds, depending on the temperature of the device and the length of the column utilized. In some embodiments, the elution time can be 45 seconds as determined using gas chromatography with a 3-meter column and a temperature program of from 170° C. to 250° C. In some embodiments, the THC signature peak can have an associated mass peak of approximately 315 m/z.

In yet additional embodiments, visual detection techniques can be used to determine the presence of THC, other drugs, or metabolites thereof in a particle sample. Visual detection techniques include any detection technique whereby the presence of THC, other drugs, or metabolites thereof can be confirmed by the naked eye, a spectroscopy technique (e.g., UV/Vis spectroscopy, fluorescence spectroscopy, and/or phosphorescence spectroscopy), and combinations thereof. In some embodiments, the method can further comprise converting the volatilized sample to a liquid sample or solid sample. In yet additional embodiments, the method can further comprise exposing the volatilized sample, the liquid sample, or the solid sample to a visualization reagent (e.g., a dye, a fluorophore, a phosphor, or a chemiluminescent agent). Such an exposure step can comprise coupling (e.g., electrostatically, covalently, or combinations thereof) components within any of these samples with the visualization reagent. In yet additional embodiments, the pH of these samples can be modified to yield a color change. In particular disclosed embodiments, visual detection techniques involve identifying a color change.

Color changes can be detected by visualizing, with the naked eye or a spectroscopic technique, a change in color, the appearance of a color, the disappearance of a color, or any combination thereof. In particular disclosed embodiments, the color change can result from a change in pH of the sample or components with the sample, the interaction of the sample or components of the sample with a visualization reagent, or combinations thereof.

Additional embodiments of the methods described herein can comprise using a chromatographic detection technique to determine the presence of THC, other drugs, or metabolites thereof in the particle samples. Such embodiments can comprise introducing the volatilized sample into an instrument suitable for chromatographic separation and identification of different components present in the sample, such as liquid chromatography, gas chromatography, or combinations thereof. Exemplary chromatographic techniques include, but are not limited to, normal-phase chromatography, partition chromatography, displacement chromatography, reversed-phase chromatography, size-exclusion chromatography, ion-exchange chromatography, and/or bioaffinity chromatography. In some embodiments, the volatilized sample can be converted to a liquid sample for analysis using liquid chromatography. In some embodiments, the volatilized sample can be introduced into a gas chromatography system for analysis. In embodiments of the methods wherein components of the particle sample are analyzed using chromatographic techniques, a chromatogram can be produced that includes different peaks with different elution times, wherein each peak/elution time typically represents a different chemical species present in the particle sample. By separating the different peaks, it is possible to determine whether a particular compound of interest is present (e.g., THC, other drugs, or metabolites thereof) based on whether or not a peak corresponding to that compound is present in the chromatogram. Elution times of peaks obtained from particle samples can be compared with peaks/elution times of reference peaks obtained from reference samples using the same, or substantially the same, parameters used to analyze the particle sample.

In particular disclosed embodiments, the methods described herein can also be used to quantify the amount of each drug present in the particle samples. In some embodiments, the amount of the drug (or drugs) present in the particle sample can be determined by using an above-described detection technique in combination with a chromatography technique. In such embodiments, the identified drugs can be quantified by assessing the amount of area under a particular peak produced by chromatographic analysis. The area under each peak in a resulting chromatogram typically is proportional, or substantially proportional, to the amount of the drug present in the particle sample. Calculations can be used to calculate the area under each peak of interest (e.g., approximate area=height of the peak above the baseline×width of the peak at half of its height). In some embodiments, peak height alone may be used to estimate the quantity of drug or THC.

Figure 3:
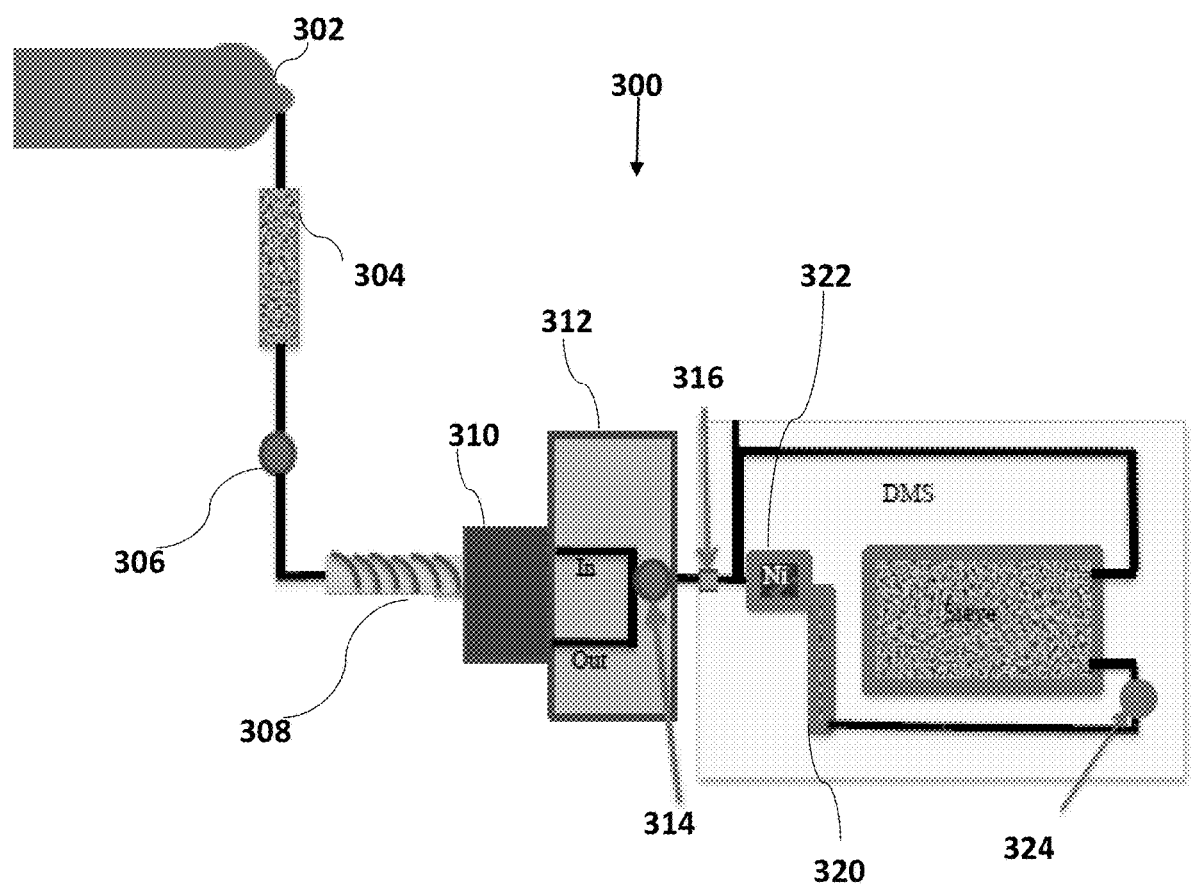
FIG. 3 is a schematic gas flow diagram showing components of a representative inductive heating-differential mobility spectrometry (IH-DMS) system.
Figure 4:
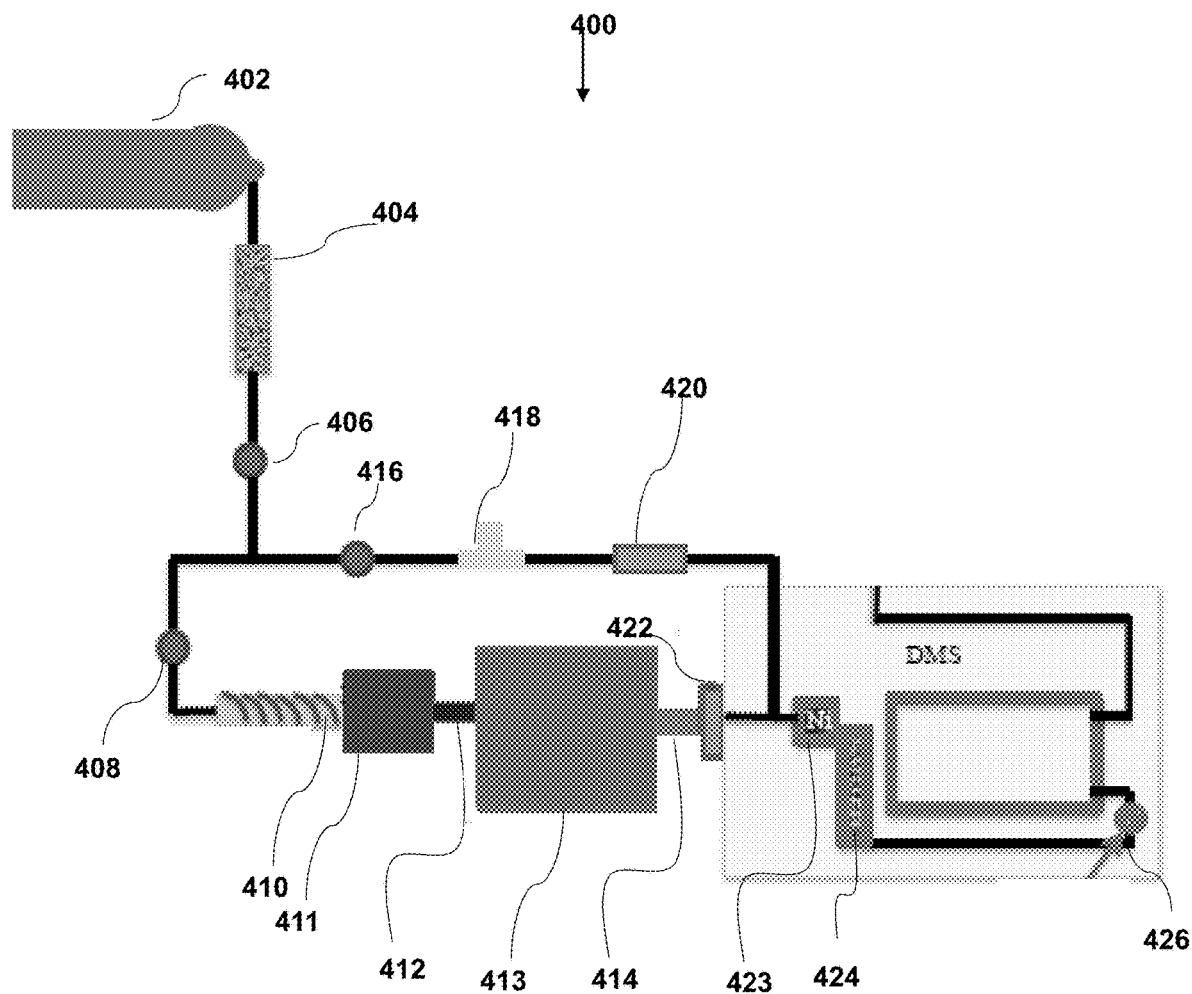
FIG. 4 is a schematic gas flow diagram showing components of a representative inductive heating-gas chromatogram-differential mobility spectrometry (IH-GC-DMS) system.

In particular disclosed embodiments, a representative method can include obtaining a particle sample from a subject by having the subject breath into a breathalyzer device or by swabbing the subject's mouth, nose, or tongue with a swab. The method can further comprise subjecting the isolated breath sample or isolated swab sample to heat using thermal desorption, which can include regular heating or inductive heating techniques. Any drugs present in the particle sample will be volatilized during the thermal desorption and present in the resulting volatilized sample. In particular disclosed embodiments, the volatilized sample is transported via a carrier gas to an ion mobility spectrometry system or a differential mobility spectrometry system that detects the presence of any drugs in the volatilized sample produced from the particle sample. In some embodiments, the differential mobility spectrometry system can be an inductive heating differential mobility spectrometry (IH-DMS) system. A representative IH-DMS system setup is illustrated in FIG. 3. With reference to FIG. 3, the system 300 can comprise any combination of the following components: a gas tank 302; a sieve component 304; a pressure gauge 306; a sample tube 308; an injection port 310; a DMS inlet 312 further comprising a membrane hole 314; an orifice 316; an ionization source 318; a DMS cell (or DMS chip) 320; another sieve component 322; and a recirculating pump 324. In some embodiments, these components are fluidly coupled together in the manner illustrated in FIG. 3. In yet additional embodiments, the differential mobility spectrometry system can be an IH-DMS system that is further coupled with a gas chromatography column. A representative IH-GC-DMS system is illustrated in FIG. 4. With reference to FIG. 4, the illustrated IH-GC-DMS system 400 includes similar components as the IH-DMS system of FIG. 3 (e.g., a gas tank 402; a sieve component 404; a pressure gauge 406; a sample tube 410; an injection port 411; an ionization source 423; a DMS cell (or DMS chip) 424; and a recirculating pump 426. System 400 further comprises a regulator 408, a GC column 413 with corresponding transfer in (412) and transfer out (414) lines, wherein the transfer out line leads to injection port 422. Additionally, a second fluid line is provided comprising a second regulator 416, an exhaust T-joint 418, and an orifice 420.

After the volatilized sample has passed through the detection device, any peaks detected by the detection technique can be viewed, such as by viewing the actual peaks in a spectrum produced by the detection technique/device or by viewing a corresponding readout provided by a screen on the device. For example, the device can comprise a screen that projects various readouts depending on the outcome of the detection steps. If drugs are present, a readout could specify the drug species present or it could simply provide a readout indicating that a drug has been "detected" or "not detected," or other such language. In yet additional embodiments, the device can indicate how much of a drug is present in the subject's system.

Methods described herein are sensitive detection methods that can be used to detect the presence of drugs at amounts as low as 5-10 ng. The methods also can be used to accurately detect whether a subject is under the influence of such drugs in a fast, reliable fashion and therefore are suitable for use in law enforcement, the public and private sector workforce, and in hospitals or veterinary clinics.

IV. Examples

Example 1

In this example, pre-inhalation and post-inhalation breath samples were obtained from 14 different volunteers. 24 sample sets total were collected and the samples included 2 to 3 pre-inhalation breath samples and 2 to 3 post-inhalation breath samples for each set. These breath samples were analyzed using a differential mobility spectrometer (DMS) and a drift tube ion mobility spectrometer (DT-IMS). Overall, over 400 spectra were obtained from pre-inhalation and post-inhalation breath of marijuana inhaling volunteers.

The volunteers were advised to achieve a high of a self-assessed level between 4 to 6 on a scale of 1 to 10. The volunteers were recruited and included both males and females between the ages of 21- to 35-years old. Breath samples were collected by having a subject breath into a collection tube for a time sufficient to provide one minute's worth of exhaled breath. The particles expelled from the subject's breath were collected on a tube comprising an absorbent material (e.g., glass wool). The analyses of the particles collected onto the absorbent material from the tubes were performed on a DMS and a DT-IMS. In some embodiments, the presence of THC was confirmed by observing a reduced mobility value of 1.07 $cm^2V^{-1}s^{-1}$ on the DT-IMS, which matched the literature values for THC. In some embodiments of pre-inhalation and post-inhalation breath samples, analysis using DMS and DT-IMS indicated that no THC was observed in pre-inhalation breath and that the presence of THC was detected from post-inhalation breath. In some embodiments, the presence of THC was detected 50% of the time. From the DT-IMS data the post-inhalation breath THC peak was of low intensity but when directly exhaled smoke samples were run the THC peak was extremely intense overloading the analysis system. This example indicates that THC can be detected by analyzing particles obtained from the breath of a subject. In some embodiments, no false positives were detected. In some embodiments, some false negatives were detected but can be corrected by adjusting the adsorption, desorption, transfer, and/or detection.

Example 2

In this example, a breath collection system was used to capture breath samples from volunteers and trap the THC-containing particle samples. The breath collection system comprised a breath mouthpiece, a protective body, and a particle-trapping component (see, for example, FIG. 1). The breath mouthpiece was a commercial FDA-approved mouthpiece originally designed for the AlcoHAWK CA2010/Avanti breathalyzer (Pleasant Prairie, Wis.). Each breath mouthpiece was individually wrapped in plastic to insure it remained sterile. The protective body was designed to protect the particle-trapping component from any outside contaminates while still allowing the breath mouthpiece to fit directly into the particle-trapping component. The protective body was a hollow 3.8 cm×3.7 cm cylinder made out of black delrin. Each end had a screw cap that could be taken off. One end cap had a hole that fit the breath mouthpiece and the other end had a showerhead design of small holes, a design feature which allowed the breath to pass from the mouth through the particle-trapping component and out of the protective body. The particle-trapping components were aluminum 0.9 cm×3.8 cm cylinders stuffed with a collecting medium, such as 0.1 g of non-treated glass wool from Fisher Scientific (Pittsburgh, Pa.) that was secured at each end by a 305 stainless 120 metal mesh, 0.001 inch wire size shaped into a 0.45 cm radius disk to hold the glass wool in place.

The thermal desorption system was constructed to thermally desorb the THC from the skin particles off of the particle-trapping component and into the instrument for analysis. The thermal desorber had two parts, a stainless steel body that held the particle-trapping component and a brass cap that screwed onto the stainless steel body connecting the carrier gas to the particle-trapping component (see, for example, FIG. 2). The stainless steel body had pipe thread that allowed it to fit onto any pipe-swagelok fitting so it could connect to either a DT-IMS or a DMS instrument. The brass cap of the thermal desorber had a female swagelok thread that attached to the carrier gas line. The whole thermal desorber was wrapped in 3 ft of HTC series rope heater from Omega (Stamford, Conn.), controlled by a Variac. This heating system maintained the thermal desorber at approximately 150° C. The heater was wrapped in ceramic ribbon insulation, and only the space where the stainless steel body met the brass cap was exposed to allow easy loading and unloading of the room temperature particle-trapping component into the hot heater.

The DMS used in this study was the hand-held JUNO® breathalyzer device from Chemring Detection Systems (North Carolina, N.C.). A summary of the operating conditions can be found in Table 1 and are described in detail below. The DMS cell was a standard differential mobility cell first developed by SEIONX and incorporated into the JUNO® breathalyzer device. With this design, the dispersion voltage ($V_d$) could be scanned from 400 V to 1000 V, while the compensation voltage ($V_c$) could be scanned from −40 V to +10 V. The gap between the electrodes was fixed at 0.508 mm (±10%), generating a field in the gap from 38.52 $T_d$ to 96.31 $T_d$.

TABLE 1

| Operating conditions for the DMS | |
|---|---|
| $V_d$ scan range | 4000 V to 10,000 V |
| $V_c$ scan range | −40 V to +10 V |
| DMS electrode gap | 0.508 mm ± 10% |
| Carrier gas | Nitrogen |
| Carrier gas temperature | 100° C. |
| Transfer line temperature | 150° C. to 200° C. |
| Sample gas | Laboratory air |
| Sample inlet pressure | 62 kPa |
| Buffer gas | Laboratory air |
| Ionization source | $Ni^{+63}$ |

The pneumatics of the instrument had two loops, the buffer gas loop and the sample gas loop. The buffer gas loop provided the DMS cell with clean, continuous buffer gas (air). After the buffer gas exited the DMS cell it entered a carbon adsorption tube to adsorb the sample that had been analyzed. Next, the buffer gas entered a recirculation pump and was then pushed through a molecular sieve to reduce the moister content and finally through a second carbon filter before being swept back to the entrance of the DMS cell. The recirculating pump was active at all times when the DMS was turned on. The latch valves were used to maintain a set internal moisture level; for this example, the latch valves were left open and the DMS was run with dry air only.

When the sample pump was turned on, the gaseous sample was drawn through the DMS entrance such that it came in contact with a silicon membrane. The silicon membrane separated the sample gas loop from the buffer gas loop. When a sample impinged upon the membrane, the sample would diffuse through it and then be picked up by the buffer gas and transported into the DMS cell for analysis. The rest of the sample gas and the sample were then transported through the sample gas pump and to the exit of the instrument. When the cap was placed on the instrument, both the exit and entrance to the instrument were sealed and the sample gas formed a continuous loop with the sample gas at the exit being directed back through the entrance of the instrument.

The sample inlet system was maintained at a temperature of 50° C. and an internal pressure of 62 kPa, which was maintained by the breather restrictor located between the charcoal sieve and the back of the membrane before the ruby orifice in the pneumatic line.

A carrier gas of high purity nitrogen was flowed through a flamed copper gas line that was heated to 100° C. by a 12-ft HTC series rope heater, controlled by a Variac. This carrier gas was used to move the compounds of interest from the particle-trapping component through the heated transfer line, also heated by 3-ft of HTC series rope heater set between 150° C. to 200° C., to the DMS for detection.

The DMS was connected to a laptop computer by a three-port power, communications, and RS-232 cable. The DMS was operated by General Dynamics Basic JUNO™ Expert software. All data was analyzed using Microsoft Excel or OriginPro 8.5.

In some embodiments, a stacked ring drift tube stand-alone ion mobility spectrometer was used and operated in the positive ion detection mode. A voltage of 7000 V was applied to the first ring of the drift tube by a Bertan high voltage power supply (Hauppauge, N.Y.) to create an electric field of 660.38 V/cm across the 10.6 cm long drift tube. The conditions under which the ion mobility spectrometer was operated are summarized in Table 2. The drift tube was heated by two 300 W Watlow cartridge heaters (St. Louis, Mo.), which were inserted into the outer metal heating case. The temperature of the drift tube was controlled using an Omega CN9000A temperature controller (Stamford, Conn.). The temperature of the drift tube was set to 150° C. throughout these experiments, and was checked daily by a thermocouple used in conjunction with a Fluke179 True RMS Multimeter (Everett, Wash.). The instrument was operated at atmospheric pressure (ranging between 680-700 torr), which was measured and recorded during each run. Daily fluctuations in the temperature and pressure were taken into account when the reduced mobility values were calculated.

TABLE 2

Operating conditions for the DT-IMS

| | |
|---|---|
| Drift gas flow rate | 1 L/min |
| IMS tube temperature | 150° C. |
| IMS first ring potential | 7000 V |
| IMS electric field | 660.38 V/cm |
| Ionization source | $Ni^{63}$ |
| Carrier gas flow rate | 0.3 L/min |

The drift and carrier gases were both high purity compressed air manually regulated by Omega FL-3803ST rotameters (Stamford, Conn.). The drift gas was introduced into the drift tube by a gas inlet in the Faraday plate detector, which had a gas showerhead ring design. The carrier gas flowed across the sample and through a heated transfer line into a sample ring positioned in front of the Bradbury-Nielson gate in the drift tube.

The signal coming off of the Faraday plate detector was converted to spectra by the in-house programed LabView software 2009 Professional Development System (National Instruments, Austin, Tex.). The electronics were controlled using LabView (National Instruments, Austin, Tex.) in-house programed software.

THC was obtained as an analytical drug standard from Sigma Aldrich (Missouri, USA). Although THC is a schedule 1 narcotic, the Exempt Chemical Preparations List approved by the Drug Enforcement Administration Office of Diversion Control of the Drug and Chemical Evaluation Section permits the use of analytical standard solutions for the development of analytical methods. THC was received as a 1 mg/mL solution in methanol as the solvent. It was diluted to various concentrations ranging from 1 mg/mL to 1 ng/mL with HPLC grade methanol from EMD chemicals (Darmstadt, Germany).

THC standards were tested in the DMS and the DT-IMS by thermal desorption introduction. The THC standards in the DMS were loaded into a heated sample chamber and the THC standard vapor was then directed with a low flow nitrogen carrier gas (0.3 mL/min) down the transfer line to the DMS for detection. THC standard concentrations ranged from 50 μg of THC to 500 μg of THC, however the entire THC concentration was not introduced into the DMS for analysis all at once due to the low vapor pressure of THC and the slow heating of the sample over time. The DMS recorded scans from a $V_d$ of 400 V to 1000 V and a $V_c$ of −40 V to +10 V. The same sample introduction method described above was used for the solvent blank, which consisted of pure methanol only.

The THC standard was introduced into the DT-IMS by thermal desorption from the particle-trapping agent. The reduced mobility value ($K_0$) of THC was used to identify the proper product ion peak. According to the literature the $K_0$ value of THC is $1.06 \pm 0.02$ $cm^2V^{-1}s^{-1}$. The concentration of the THC standard ranged from 50 μg to 110 μg, and similar to THC introduced into the DMS, the amount of THC standard vapor introduced into the DT-IMS will be orders of magnitude lower than what was loaded onto the particle-trapping component. First the THC standard was loaded into the particle-trapping component directly by pipette. Then the particle-trapping component doped with the standard was allowed to dry on the bench top for five minutes before being loaded into the pre-heated (e.g., 150° C. to 200° C.), thermal desorber. The compressed air carrier gas was turned off until the particle-trapping component was completely loaded and the system software was started. After the particle-trapping component was loaded and the system software was started the carrier gas was turned on at a flow rate was approximately 0.3 mL/min. The IMS recorded 100 averages over 10 iterations each scan window was 40 ms. The $K_0$ value of the THC peak was calculated and compared to literature $K_0$ values to confirm identity.

Volunteers were recruited from the Washington State University adult student population. They consisted of males and females ranging in ages from 21 to 35. The volunteers were asked to purchase "Blue Dream" cannabis which contained ~22.8% THC per gram. The breath collection was performed at the volunteer's private residence. Before breath collection each volunteer was asked to sign a consent form and the breath collection process was verbally explained to them. The volunteers were also asked to fill out a survey where they were asked to list their eating, drinking, and oral hygiene habits for the past 12 hours. Each particle-trapping component was blown into for 1 minute to collect the breath sample. Two or three samples were collected from each volunteer, both before and after inhalation.

The TD-DMS was scanned throughout the full $V_d$-$V_c$ range for THC response. The THC standard did not overload the system since a reactant ion peak (RIP) was still seen. The RIP was mainly from the methanol solvent that made up the THC standard. Separation between the RIP and the THC standard was seen at a $V_d$ of 500 V to $V_d$ of 1000 V with the most intense THC signal from a $V_d$ of 500 V to a $V_d$ of 750 V with a maximum intensity of 0.114 above baseline. As the $V_d$ was increased the THC signal shifted to a more positive $V_c$. For example, at a $V_d$ of 700 V THC can be seen at a $V_c$ of 1 V while at a $V_d$ of 1000 V THC can be seen at a $V_c$ of 3 V. Due to the slow heating of the THC standard, some sample was moved through the TD-DMS before the software was started. Consequently, the THC concentration detected by the TD-DMS was orders of magnitude smaller than the amount introduced. Since the TD-DMS was not a sealed system, small shifts in THC $V_d$ or $V_c$ response as a function of the overall system were expected. There was no $V_d$ or $V_c$ shift due to the increase of THC concentration, but the peak intensity did increase as the THC concentration was increased. A strong THC standard signal allowed optimization of the TD-DMS settings for the best possible detection of THC from breath.

Figure 5:
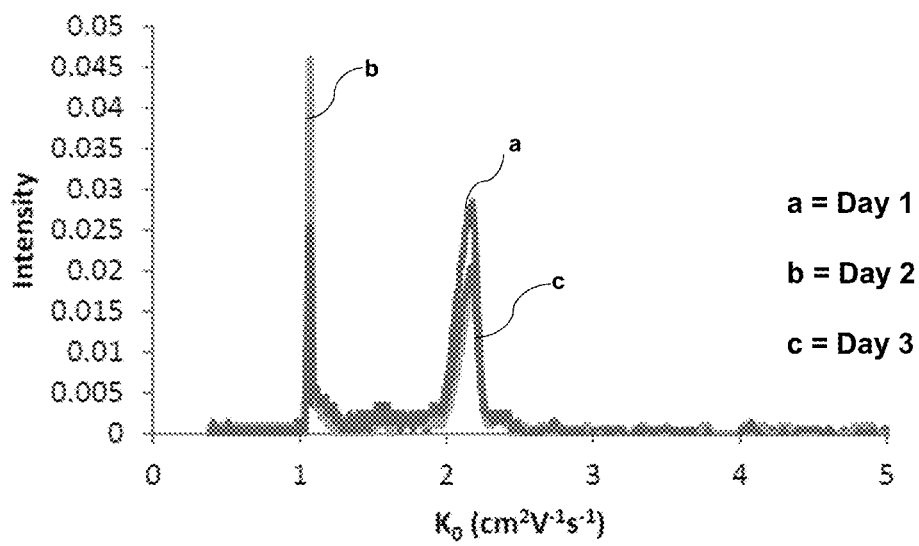
FIG. 5 is a combined spectrum showing results from analyzing a drug standard on three different days using thermal desorption coupled with drift tube ion mobility spectrometry.

The THC standard also gave a high intensity reproducible response on the TD-DT-IMS. The THC standard was applied to a particle-trapping component and was then introduced by thermal desorption into the DT-IMS. The THC standard was tested across three different days with THC standard concentrations' ranging from 50 μg to 110 μg. FIG. 5 shows the THC standard response with $K_0$ value on the x-axis and intensity on the y-axis. Each spectrum represents a THC standard spectrum from a different day. The $K_0$ values for the THC standards are 1.073 $cm^2V^{-1}s^{-1}$ for Day 1, 1.071 $cm^2V^{-1}s^{-1}$ for Day 2, and 1.071 $cm^2V^{-1}s^{-1}$ for Day 3. This gave an average THC $K_0$ value of 1.072±0.001 $cm^2V^{-1}s^{-1}$, which agrees with the literature value of 1.06±0.02 $cm^2V^{-1}s^{-1}$.

Once the ability to detect THC standard by thermal desorption on the DMS was confirmed, clean non-THC containing human breath samples were collected on to the particle-trapping agents and analyzed. Clean human breath (without inhaling cannabis smoke) was blown onto the particle-trapping component. The volunteer had not eaten or performed any oral hygiene within 4 hours of the application of breath to the particle-trapping component. For the breath detection in the DMS a smaller $V_d$ range of 600 V to 800 V was used. This was the area with the best separation from the RIP peak while maintaining sufficient THC peak intensity. The THC peak intensity is important because there may be potential interferences due to the complex breath sample matrix. The clean human breath did not show any interference with THC detection region, $V_d$ of 700 V and a $V_c$ range of −40 V to +10 V for which THC was previously detected.

Other common interferences were also tested on human breath to see if they would cause any interference in THC detection. Human breath containing cigarette smoke, mouthwash vapors, and coffee vapors were all tested on the DMS to see if the response would be similar to THC. All of these common possible interferences showed peaks at lower $V_c$ values than THC, which was detected at a $V_c$ of 1 V and a $V_d$ of 700 V. Therefore these common contaminates should not hinder in detection of THC especially if the $V_c$ range was decreased to scan only from −5 V to +10 V. This limited $V_c$ range would only focus on THC, and would not scan a voltage range low enough to detect coffee, cigarette smoke, or mouthwash.

Clean, non-THC containing, human breath samples were also collected on to the particle-trapping components and analyzed in the TD-DT-IMS. Any interference detected on clean human breath could be characterized by their $K_0$. It was found that clean human breath contained no interferences that would affect the detection of THC. This was confirmed by comparing the $K_0$ values from the breath samples to THC standards previously analyzed. The only response the clean human breath had on the TD-DT-IMS spectrum was a broadening of the RIP peak at a $K_0$ value of 2.19±0.02 $cm^2V^{-1}s^{-1}$ and the addition of a small peak at a $K_0$ value of 2.38±0.02 $cm^2V^{-1}s^{-1}$. The RIP peak is mainly affected by the amount of moisture in the system. Human breath samples contain high amounts of moisture and other low mass volatile organic compounds that have similar mobilities as the RIP; these could have caused the peak broadening and the double peak, but their identities cannot be confirmed without a mass spectrometer.

Volunteers were recruited to provide breath samples both before and after inhaling cannabis to compare the response of pre-inhalation (no THC) breath and post-inhalation (THC) breath. There were 15 volunteers, 2 females and 13 males. The volunteers smoked in inhalation groups with 2 to 6 volunteers in a group. Between March 2015 to May 2015, 24 sample sets, which consisted of two or three pre-inhalation samples and two or three post-inhalation samples, were collected. About 400 spectra were collected including both pre-inhalation and post-inhalation breath samples. These sample sets were split between the TD-DT-IMS and TD-DMS for analysis. The TD-DT-IMS was used to process 66% of the samples, while the TD-DMS processed 34%.

Figure 6:
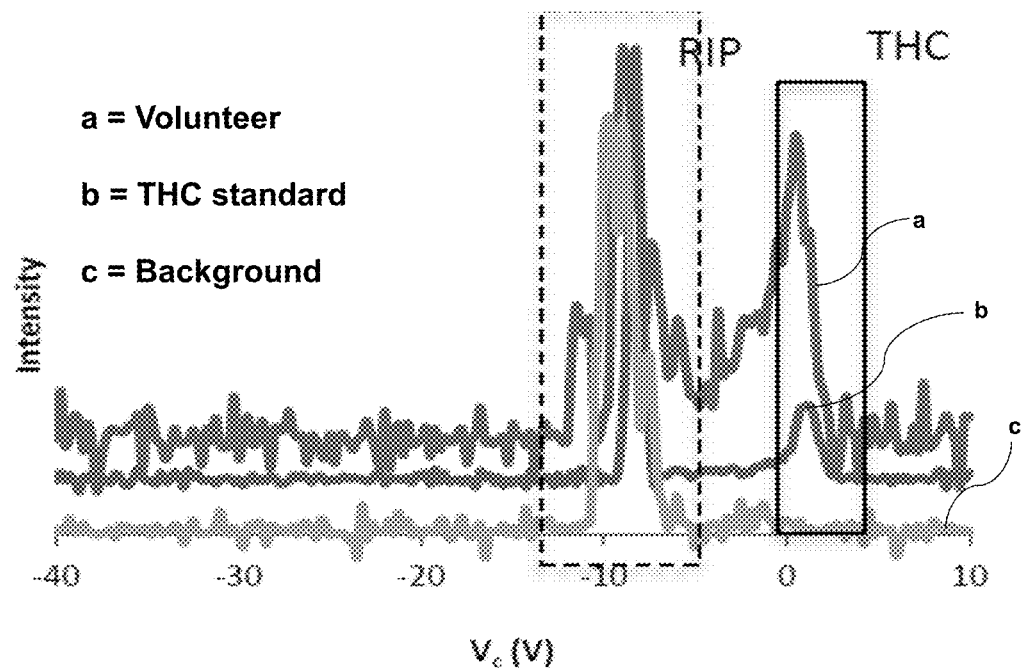
FIG. 6 is a combined spectrum showing results obtained from using a representative detection technique combining thermal desorption with differential mobility spectrometry to analyze a particle sample obtained from a subject's breath after the subject had inhaled/ingested cannabis.

Each spectrum in both the TD-DMS and TD-DT-IMS data array was individually checked to insure accurate THC identification. FIG. 6 shows a typical TD-DMS spectrum for a post-cannabis inhalation breath sample. This is compared to the THC standard for visual confirmation that the sample contains THC. It was found that THC detected from post cannabis inhalation breath had an average $V_c$ value of 0.48±0.27 V at a $V_d$ of 700 V; this was from 28 post-inhalation spectra that positively identified THC. This is within the range of the THC standard, which had a $V_c$ of 1±0.75 V at a $V_d$ of 700 V.

Figure 7:
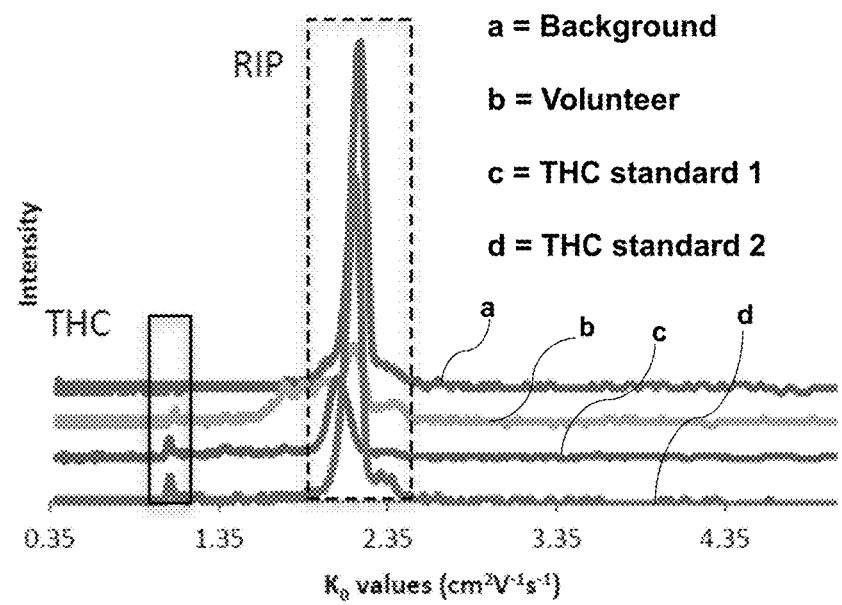
FIG. 7 is a combined spectrum showing results obtained from using a detection technique combining thermal desorption with drift tube ion mobility spectrometry to analyze a particle sample obtained from a subject's breath after the subject had inhaled/ingested cannabis.
Figure 8:
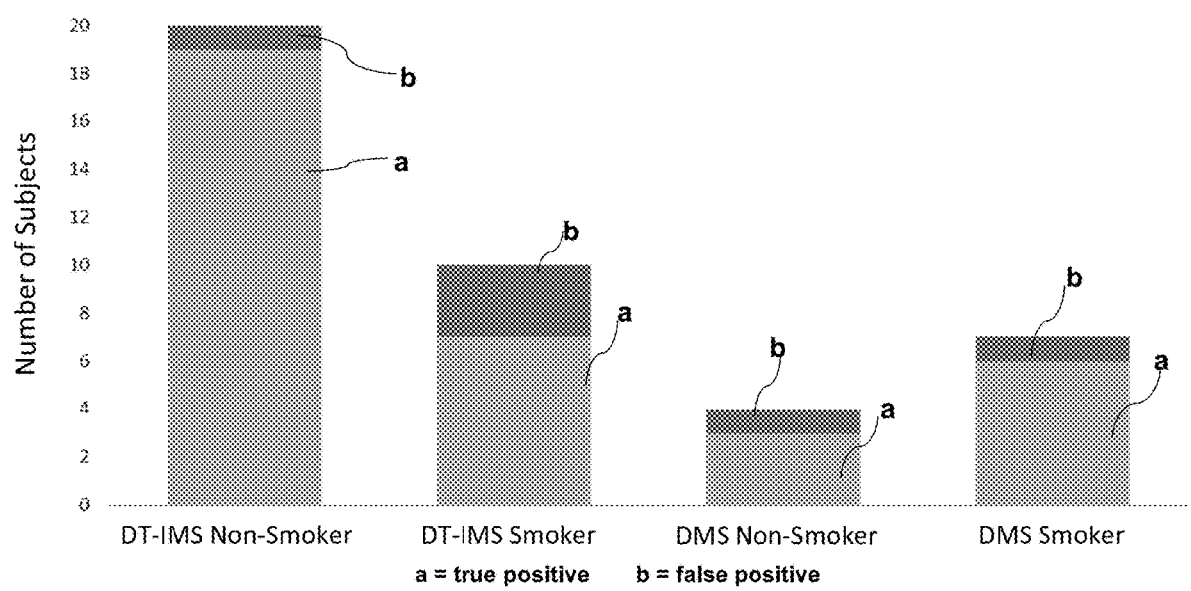
FIG. 8 is a bar graph showing results obtained from using a representative detection technique combining thermal desorption with different ion mobility spectrometry to analyze particle samples, wherein each bar represents a different analysis system (DMS or DT-IMS) or sample (particles obtained from breath, pre- or post-inhalation of cannabis) and the number of subjects tested is provided by the y-axis.

A typical DT-IMS $K_0$ spectrum for post cannabis inhalation breath is displayed in FIG. 7 with THC standard spectra for visual comparison. From 30 post cannabis inhalation breath spectra the average THC $K_0$ value was 1.08±0.01 $cm^2V^{-1}s^{-1}$. This is within the 1.06±0.02 $cm^2V^{-1}s^{-1}$ literature value. The overall results of THC detection from breath samples of cannabis smokers are displayed in Table 3. This table lists the volunteer's identification number, and the instrument with which the sample was analyzed. Not every volunteer provided a pre-inhalation sample for both instruments; these were indicated with an N/A under the corresponding column. If the pre-inhalation sample showed a peak indicating THC was detected it is listed as a false positive, and is listed as a true positive if THC was detected from the post-cannabis inhalation sample and as a false negative if no THC was detected. Out of fourteen samples, there was only one false positive from the pre-inhalation breath and one false negative from the post-cannabis inhalation breath on the TD-DMS, giving it an overall detection rate of 81%. The TD-DT-IMS initially gave one false positive for pre-inhalation breath and two false negatives for post-inhalation breath with an overall detection rate of 85% from a sample set of twenty. The true negative ("b") and true positive ("a") values for each system for pre and post-inhalation samples are displayed in the bar graph in FIG. 8.

TABLE 3

| Volunteer # | instrument | Pre-inhalation breath | Post-inhalation breath |
| --- | --- | --- | --- |
| 4 | DMS | N/A | YES |
| 2 | DMS | N/A | NO |
| 5 | DMS | NO | YES |
| 6 | DMS | NO | YES |
| 7 | DMS | NO | YES |
| 2 | DMS | N/A | YES |

TABLE 3-continued

| Volunteer # | instrument | Pre-inhalation breath | Post-inhalation breath |
|---|---|---|---|
| 9 | DMS | YES | YES |
| 5 | DT-IMS | N/A | YES |
| 5 | DT-IMS | N/A | NO |
| 6 | DT-IMS | N/A | YES |
| 7 | DT-IMS | N/A | YES |
| 11 | DT-IMS | NO | YES |
| 12 | DT-IMS | NO | YES |
| 11 | DT-IMS | YES | YES |
| 12 | DT-IMS | NO | NO |
| 3 | DT-IMS | NO | YES |
| 13 | DT-IMS | NO | YES |

Each volunteer that gave a false positive was verbally questioned; this was to check that the information they gave on their breath survey was correct and they did not smoke cannabis in the past 24 hours. One volunteer admitted during this verbal questioning that cannabis was smoked 4 hours prior to breath collection. This shows that a TD-DT-IMS has to potential to detect THC on breath hours after use. This admission to inhaling cannabis prior to the pre-inhalation breath collection also accounts for the false positive seen in the TD-DT-IMS pre-inhalation statistics. Therefore the TD-DT-IMS actually had no false positives for pre-inhalation breath, and nine true positives for post cannabis inhalation breath making the TD-DT-IMS's actual overall detection rate 89%, rather than 85%.

Example 3

In this example, particle samples obtained from subjects' breath were evaluated to determine potential interfering chemicals in the breath samples. A breath collector device comprising a particle-trapping component as described herein was used along with a thermal desorption system as described herein. Drift tube IMS was used as the detection technique. The DT-IMS was used and operated in the positive ion detection mode where a voltage of 7000 V was applied to the first ring of the drift tube by a Bertan high voltage power supply (Hauppauge, N.Y.) to create an electric field of 660.38 V/cm across the 10.6 cm long drift tube. The drift tube was heated by two 300 W Watlow cartridge heaters (St. Louis, Mo.), which were inserted into the outer metal heating case. An Omega CN9000A temperature controller (Stamford, Conn.) regulated the temperature of the drift tube. The temperature of the drift tube was set to 150° C. throughout this example, and was checked daily by a thermocouple used in conjunction with a Fluke 179 True RMS Multimeter (Everett, Wash.). The instrument was operated at atmospheric pressure (ranging between 680-700 torr), which was measured and recorded during each sample run. Daily fluctuations in the temperature and pressure were taken into account when the reduced mobility values were calculated.

The drift and carrier gases were both high purity compressed air manually regulated by Omega FL-3803ST rotameters (Stamford, Conn.). A gas inlet in the Faraday plate detector which had a showerhead ring design introduced the drift gas into the drift tube. The sample ring was positioned in front of the Bradbury-Nielson gate in the drift tube. A carrier gas was sent across the sample and through a heated transfer line into a sample ring to introduce the sample into the drift tube. The conditions under which the DT-IMS was operated were the same as those summarized in Table 2 above.

THC standard was directly applied to the particle-trapping component, then it was allowed to dry on the bench top for five minutes before being loaded into the approximately 200° C. TD-DT-IMS for analysis. The THC peak in the spectrum was identified by the reduced mobility value ($K_0$) and compared to the literature $K_0$ value for THC, 1.06±0.02 $cm^2V^{-1}s^{-1}$. The concentration of the THC standard used ranged from 50 μg to 110 μg. The amount of THC standard vapor introduced into the TD-DT-IMS was orders of magnitude lower than what was loaded onto the particle-trapping component. This was due to the secondary heating of the particle-trapping component by thermal desorption, a process which did not allow for all of the THC standard to be desorbed at the same time. The compressed air carrier gas was turned off until the particle-trapping agent was completely loaded and the system software was started, then the carrier gas was turned on at a flowrate was approximately 0.3 mL/min. The IMS recorded 100 averages over 10 iterations; each scan window was 40 ms. Subjects were selected as described in other examples provided herein.

Figure 9:
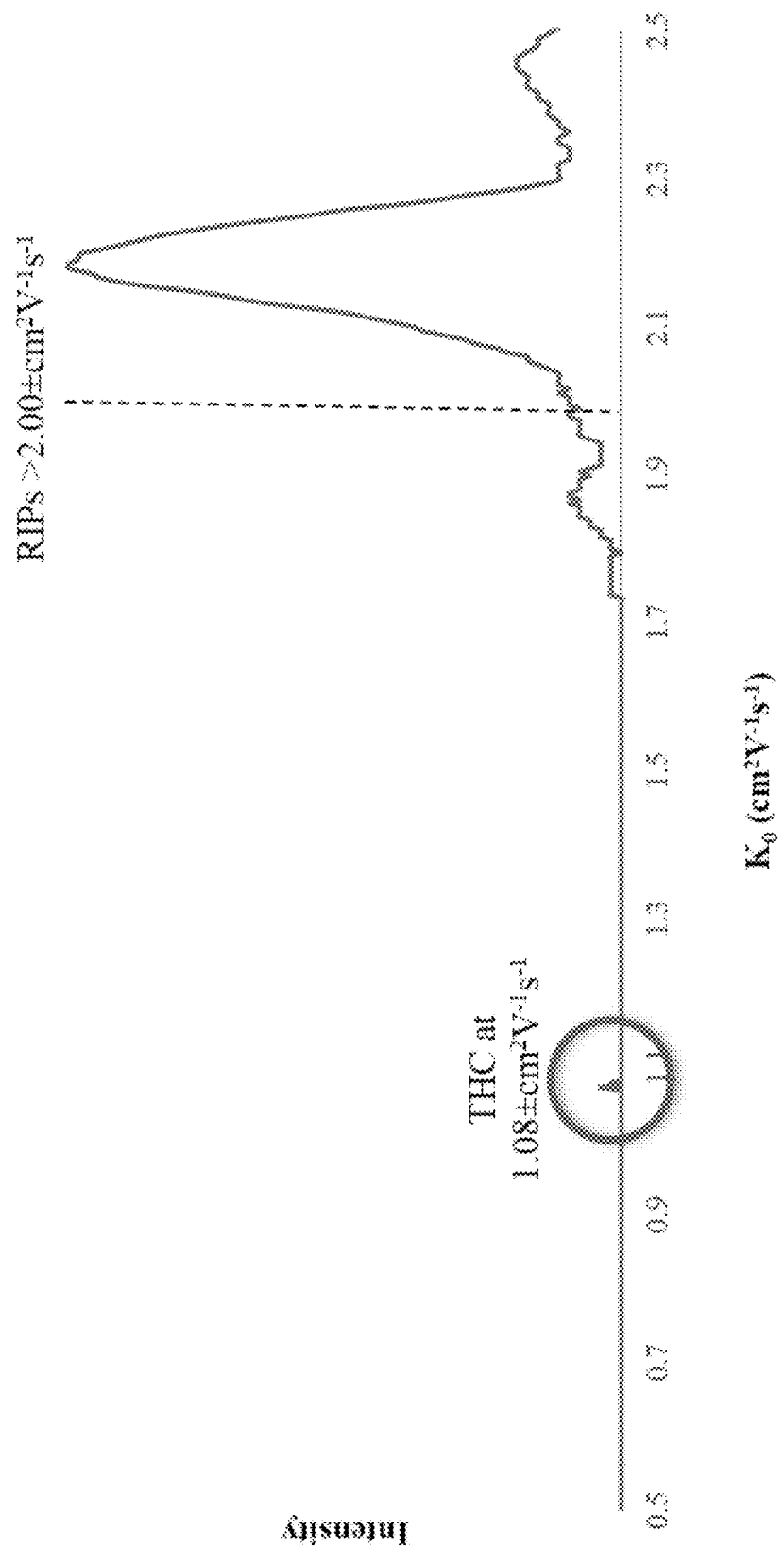
FIG. 9 is a spectrum obtained from analyzing particles obtained from post-inhalation cannabis breath with positive detection of THC at an average $K_0$ value of 1.08±0.01 $cm^2V^{-1}s^{-1}$ (circled); the $K_0$ value on the x-axis is displayed from 0.5 $cm^2V^{-1}s^{-1}$ to 2.5 $cm^2V^{-1}s^{-1}$ and the intensity is on the y-axis; the reactant ion peaks (RIPs) were detected at $K_0$ values greater than 2.00 $cm^2V^{-1}s^{-1}$; and the dotted line represents maximum $K_0$ value used when identifying peaks commonly detected in human breath.

THC could be detected from post cannabis inhalation breath by TD-DT-IMS. FIG. 9 shows an example of human breath with a true positive detection for THC where THC is circled on the plot with a $K_0$ value of 1.08±0.01 $cm^2V^{-1}s^{-1}$. In a plot with intensity on the y-axis and $K_0$ ranging from 0.5 $cm^2V^{-1}s^{-1}$ to 2.5 $cm^2V^{-1}s^{-1}$ on the x-axis it is very difficult to identify all of the other common peaks detected from human breath especially any that are of a scale similar to THC. Though THC seems small in FIG. 9, it is approximately ten times the signal to noise in this spectrum. To better identify peaks that are of a similar scale as THC the $K_0$ range on the x-axis was limited to 0.5 $cm^2V^{-1}s^{-1}$ to 2 $cm^2V^{-1}s^{-1}$. This x-axis parameter limitation eliminated three commonly detected peaks, two were the RIPs, which decreased the x-axis so the commonly detected peaks from human breath response were easier to visually identify.

Figure 10:
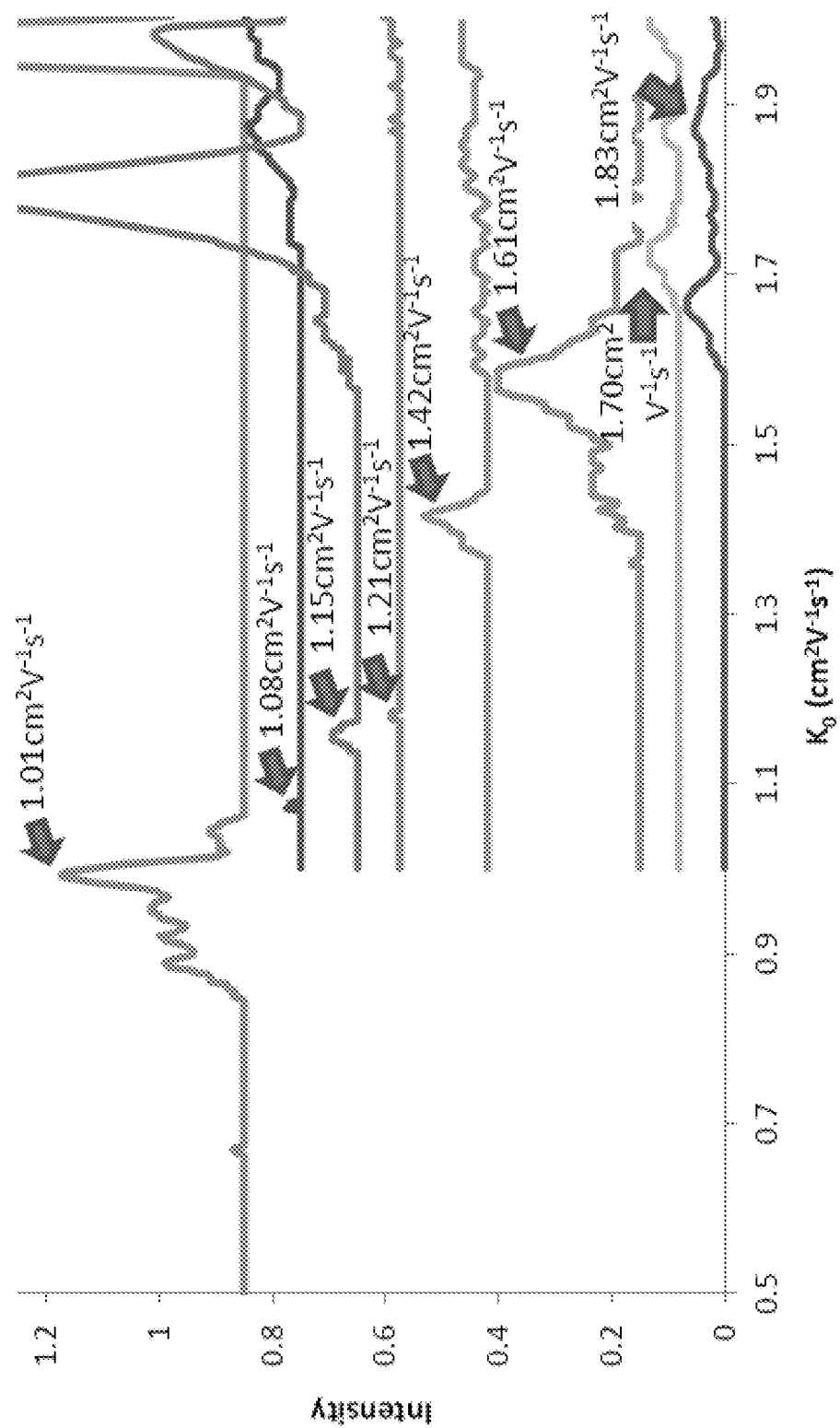
FIG. 10 is a graph showing eight commonly detected peaks from particle samples obtained from pre-inhalation and post-inhalation breath; THC at a $K_0$ value of 1.08±0.01 $cm^2V^{-1}s^{-1}$ was detected in post cannabis inhalation samples; arrows are used to indicate the other common peaks detected and the average $K_0$ value is provided.

Out of 132 pre-inhalation and post-inhalation human breath spectra 11 common peaks were detected. For a peak to be considered as a potential interferent it must have been detected in more than three spectra, and the peak intensity had to be at least three times the signal to noise ratio (3σ). In order to view the common detected peak from human breath that were on a similar scale as THC (approximately 10σ) the x-axis was set to a maximum $K_0$ value of 2 $cm^2V^{-1}s^{-1}$, this eliminated three of the eleven common peaks detected. FIG. 10 displays the nine most commonly detected peaks from human breath by the TD-DT-IMS. The spectra in FIG. 10 were normalized to a 0-1 range on the intensity axis and all the spectra experienced 3-point smoothing. An arrow and the corresponding average $K_0$ value point out the common peak detected from human breath in each spectrum. Any other shoulder, tailing, or additional peaks in the spectra are not reproducible or are not 3σ; as such they are not part of the common peaks detected from human breath. The $K_0$ ranges of each spectrum were truncated if the $K_0$ of the common peak was above 1.08 $cm^2V^{-1}s^{-1}$. Most of the common peaks detected from human breath in FIG. 10 were detected in more than one volunteer, and were detected in both pre-inhalation and post-inhalation breath samples.

The suspected causes of the eleven common peaks detected from human breath are listed in Table 4. Each $K_0$ value has a standard deviation and list of suspected causes for the peak. These suspected causes were classified according to gender, substances that were eaten or drank, tobacco use, or cannabis use. The amount of occurrence is the percentage of the peak detected due to the suspected cause verses the total number of times the suspected cause occurred. For example, one of the suspected causes for the peak with a $K_0$ value of 1.15 $cm^2V^{-1}s^{-1}$ was a female attribute. The 1.15 $cm^2V^{-1}s^{-1}$ peak was detected in three breath samples provided by females, there were only five female breath samples collected overall, hence 60%. From this information suspected causes of the common peaks detected can be investigated.

TABLE 4

| Average $K_0$ ($cm^2V^{-1}s^{-1}$) | Standard Deviation | Suspected Cause of Common Breath Contaminate Peaks | Amount of Occurrence |
|---|---|---|---|
| 1.01 | 0.01 | Male attribute | 2% |
| 1.08 | 0.01 | Smoking cannabis | 95% |
| 1.15 | 0.02 | Female attribute | 60% |
|  |  | Milk | 37% |
| 1.21 | 0.02 | Male attribute | 2% |
|  |  | Meat | 18% |
| 1.42 | 0.02 | Tobacco product | 19% |
|  |  | Male attribute | 17% |
| 1.61 | 0.04 | Tobacco product | 7% |
|  |  | Male attribute | 6% |
| 1.70 | 0.04 | Smoking cannabis | 23% |
| 1.83 | 0.05 | Male attribute | 5% |
|  |  | Meat | 5% |
| 1.83 | 0.05 | Male attribute | 5% |
|  |  | Meat | 5% |
| 2.01 | 0.07 | Meat | 11% |
|  |  | Non-cannabis smokers | 18% |
| 2.20 | 0.02 | RIP 1 | N/A |
| 2.41 | 0.04 | RIP 2 | N/A |

Three of the common peaks detected could be positively identified by their mobility values. The peak with a $K_0$ value of 1.08±0.01 $cm^2V^{-1}s^{-1}$ was confirmed to be THC by comparison of the $K_0$ value with a THC standard and comparison to the literature value for THC, 1.06±0.02 $cm^2V^{-1}s^{-1}$. The THC peak was detected in 95% of the post inhalation breath samples. None of the common peaks detected from human breath overlapped with the THC $K_0$ value of 1.08±0.01 $cm^2V^{-1}s^{-1}$. The closest peak was found at 1.15±0.02 $cm^2V^{-1}s^{-1}$, which was a 0.04 $cm^2V^{-1}s^{-1}$ difference. The two RIPs had $K_0$ values of 2.20±0.02 $cm^2V^{-1}s^{-1}$ and 2.41±0.04 $cm^2V^{-1}s^{-1}$ respectively. RIP peaks are ionized water clusters and can vary in intensity and $K_0$ value day-to-day depending on the lab environment since the drift tube was not a sealed system. The RIPs peaks detected at $K_0$ values of 2.20±0.02 $cm^2V^{-1}s^{-1}$ and 2.41±0.04 $cm^2V^{-1}s^{-1}$ were the same as the RIP peaks detected in the TD-DT-IMS system backgrounds. The RIP peaks were commonly detected in the system background, calibrations, along with most of the non-inhalation and inhalation spectra. The eight other peaks commonly detected from human breath could not be identified without the TD-DT-IMS coupled to a more comprehensive analysis method, like mass spectrometry, which would provide more information about the characteristics of the ion with that mobility value.

Example 4

The particle-trapping component used in this study was a glass tube produced by Triton Systems Inc. (Chelmsford, Mass.) configured to comprise a collecting medium, such as 0.1 g of polymer-coated steel wool packed in. The glass tubes were 5.1 cm long×1 cm OD×0.6 cm ID and were provided by Triton Systems Inc.

The breath collection device was made by Chemring Detection Systems (Charlotte, N.C.). This instrument was used for breath collection onto the particle-trapping component only, not for breath analysis. The particle-trapping component fit into an opening in the breath collection casing printed from a three-dimensional printer. Breath mouthpieces were fitted onto the breath collector component in line with the particle-trapping component so that breath was blown through the breath mouthpiece into the particle-trapping component. The sensor inside the breath collection device was powered by a 9 V battery. The breath collector sensor measured the pressure on the backside of the particle-trapping component and alarmed either after a pressure above 150 torr was reached or after 10 seconds had passed.

The triton desorption system was made by Triton Systems Inc. This system inductively heated the polymer coated steel wool particle-trapping component by applying a voltage to a copper coil that wrapped around the particle-trapping component glass tube. The heating cycle varied for the DMS (Table 5) and the GC-DMS (Table 6). Scripts written by Chemring Detection Systems used lab view software to control the heating cycles for each instrument.

TABLE 5

IH-DMS Operating Conditions

| DMS | |
|---|---|
| Dispersion Voltage | 700 V |
| Compensation Voltage Range | −40 V to +10 V |
| Carrier Gas | Nitrogen |
| Oven Temperature | 200° C. |
| Cell Pressure | ~7.6 PSI |
| Cell Temperature | 50° C. |

| Triton Heater | |
|---|---|
| Initial Pulse | 2500 ms |
| Number of Cycles | 5 |
| Cycle Period | 500 ms |

TABLE 6

RI-GC-DMS Operating Conditions

| DMS | |
|---|---|
| Dispersion Voltage | 700 V |
| Compensation Voltage Range | −40 V to +10 V |
| Carrier Gas | Nitrogen |
| Cell Pressure | ~7.6 PSI |
| Cell Temperature | 50° C. |

| GC | | |
|---|---|---|
| Ramp (° C./min.) | Temperature(° C.) | Hold (sec.) |
| 0 | 60 | 5 |
| 500 | 120 | 10 |
| 500 | 250 | 30 |

| Triton Heater | |
|---|---|
| Initial Pulse | 2500 ms |
| Number of Cycles | 3 |
| Cycle Period | 1000 ms |
| Duty Cycle | 50% |

| Transfer Lines | |
|---|---|
| Oven | 200° C. |
| Transfer Line-GC In | 250° C. |
| Transfer | 250° C. |
| Inlet | 200° C. |

With this design, the gap between the electrodes was fixed at 0.508 mm (±10%), generating a field in the gap from 38.52 Td to 96.31 Td. The dispersion voltage ($V_d$) was scanned from 400 V to 1000 V, and the compensation voltage ($V_c$) was scanned from −40 V to +10 V. The internal pressure of 62 kPa was maintained by the breather restrictor located between the charcoal sieve and the back of the membrane hole before the ruby orifice seen in FIG. 3. The samples were ionized by a 2.5 mCi Nickel-63 ionization source.

The sample was introduced by a nitrogen carrier gas after inductively heating a particle-trapping agent interfaced to the oven in front of the DMS system (FIG. 3). The carrier gas was first passed through a molecular sieve to reduce the moisture content. Then a pressure gauge was set to 20 PSI or a flow rate of ~270 mL/min. The particle-trapping component was fitted onto the gas line by airtight swagelok fittings. The inductive heater was coiled into a cylinder that slipped around the glass particle-trapping component. The other end of the particle-trapping component was secured to the oven by airtight swagelok fittings. The oven was heated to 200° C. and the DMS inlet was secured by a small swagelok transfer line to the back of the oven. All the DMS settings are listed in Table 5.

The DMS was connected to a laptop computer and run through LabVIEW software written by Chemring Detection Systems. All data were analyzed using Microsoft Excel or OriginPro 8.5.1.

The GC-DMS used in this example was designed and built by Chemring Detection Systems (North Carolina, N.C.). The GC column was a VB-1 3 m×0.32 mm×0.1 μm controlled by a Fast Temperature Programmer, both from Valco Instruments Co. Inc. (Poulsbo, Wash.). The DMS cell used in the GC-DMS was the SIONEX cell listed previously.

The IH-GC-DMS had a very similar gas flow diagram to the IH-DMS. A carrier gas introduced the sample after inductively heating the particle-trapping component interfaced to the oven in front of the GC-DMS (FIG. 4). The nitrogen carrier gas was first passed through a molecular sieve to reduce the moisture content. Then a pressure gauge was set to 30 PSI or ~405 mL/min flowrate. The gas flow was then split into two channels; one flow contributed to the make-up gas that pressurizes the DMS and the other flow was used as the carrier gas for conveying the sample into the GC. The rate of gas flow was controlled by a 0.007 orifice restrictor (Beswick Engineering, NH), which was set to restrict the flow to 0.2 bar above ambient pressure. An exhaust T was fitted in front of the orifice to supplement the gas flow as needed before being introduced into the DMS. The carrier gas flow was also controlled by a 0.007 orifice restrictor (Beswick Engineering, NH), which was set to restrict the flow to 0.2 bar above ambient pressure. Then the particle-trapping component was fitted onto the gas line by airtight swagelok fittings. The inductive heater was coiled into a cylinder that slipped around the particle-trapping component. The other end of the particle-trapping component was secured to the oven by air tight swagelok fittings. The oven was heated to 200° C. and connected to the GC by the GC-in transfer line that was heated by a Pelican heating wire (Naples, Fla.) controlled by a Watlow RM series controller (Mason, Ohio). The GC-in transfer line was heated to 250° C. The GC column temperature ramp program set the max ramp to 250° C. over 68 seconds. The GC-transfer line out heated to 250° C. was connected to the DMS inlet that was heated to 200° C. All the IH-GC-DMS settings are listed in Table 6. The pneumatics of the DMS instrument consisted of the carrier gas and the make-up gas.

The carrier gas helped transport the sample through the DMS cell while the make-up gas provided the DMS cell with clean, continuous buffer gas (air). After the buffer gas exited the DMS cell it entered a recirculation pump and then exited the DMS by an exhaust valve.

The DMS sample inlet system was maintained at a temperature of 50° C. and an internal pressure of 62 kPa, which was maintained by the breather restrictor located between the charcoal sieve and the back of the membrane hole before the ruby orifice in the pneumatic line. The samples were ionized by a 2.5 mCi Nickel-63 ionization source.

The GC-DMS was connected to a laptop computer and run through LabVIEW software written by Chemring Detection Systems. All data were analyzed using Microsoft Excel or OriginPro 8.5.1.

The THC standard was diluted to concentrations ranging from 100 ng to 0.1 ng for both the IH-GC-DMS and IH-DMS. These standards were loaded onto a clean particle-trapping component, were allowed to dry for approximately 3 minutes on the bench top and then loaded into the analysis system with the sample side closest to the DMS for analysis.

The breath collection device collected 10 seconds of exhaled breath from a volunteer, who had not smoked cannabis, onto the particle-trapping component. These samples were tested on the IH-DMS and IH-GC-DMS to find the baseline produced by non-inhalation breath and what common peaks, if any, would be detected.

The THC standard was applied to the particle-trapping component and allowed to dry on the bench top for 3 minutes. Then the particle-trapping component was loaded into the breath collector and 10 seconds of non-inhalation breath was applied. This THC standard and breath particle-trapping component was analyzed on the IH-DMS and IH-GC-DMS to insure THC standard could be detected from the non-inhalation breath interference.

Volunteers similar to those described above were selected for this example. The volunteers were also asked to fill out a survey detailing their eating, drinking, and oral hygiene activities for the past 12 hours. The type of cannabis they were inhaling was verified and the type of inhalation device was recorded. Each particle-trapping component was blown into for 10 seconds to collect the breath sample. One sample was collected from each volunteer both before and after inhalation.

The volunteers were asked to smoke to obtain a high at a level between a 4 and a 6 on a personal self-assessment scale of intoxication ranging from 1 to 10, where 10 is the level of extreme high. After the breath samples were collected the volunteers were instructed to abstain from driving for 2 to 4 hours, and the particle-trapping components were taken back to the laboratory for analysis. Analysis was generally performed within 24 hours of sample collection.

The polymer-coated steel wool glass tube with the IH-DMS was tested with a THC standard to establish analytical figures of merit for IH desorption and DMS detection with no protective membrane. It was found that removing the membrane made the DMS more sensitive to the THC standard, reaching a limit of detection of 10 ng when directly applied to the particle-trapping component. This increased sensitivity also caused the dynamic range of this system to extend from 10 ng to 500 ng and the linear range was 50-100 ng.

Spectra from both the non-inhalation human breath and non-inhalation human breath with THC standard applied to the particle-trapping component displayed low contamination peaks and strong THC standard responses. The baseline noise response had an intensity of 5000 counts at a $V_d$ of 1000 V across the full $V_c$ scan of −40 V to +10 V. First, non-inhalation human breath was collected onto the particle-trapping component by the breath collector and analyzed with the IH-DMS. The spectrum only showed a small broad peak at a $V_c$ of 5 V at a $V_d$ of 1000 V with an intensity of 6000 counts max. Then on a clean particle-trapping component 50 ng of THC standard was applied. The THC standard response in the IH-DMS was a sharp peak at a $V_c$ of 3.69±0.15 V at a $V_d$ of 1000 V and an average intensity of 10,000 counts. Finally non-inhalation human breath was collected on particle-trapping component after 50 ng of THC standard was applied. The THC standard with non-inhalation human breath response was still a sharp peak at a $V_c$ of 3.69±0.15 V at a $V_d$ of 1000 V but at an average intensity of 9000 counts. This THC standard with non-inhalation human breath response was reproducible over days, when using different human breath samples, breath collectors, and particle-trapping components. With the removal of the membrane from the DMS additional interferences were not detected from the non-inhalation human breath that potentially would hinder the detection of THC standard at low concentrations.

Figure 11:
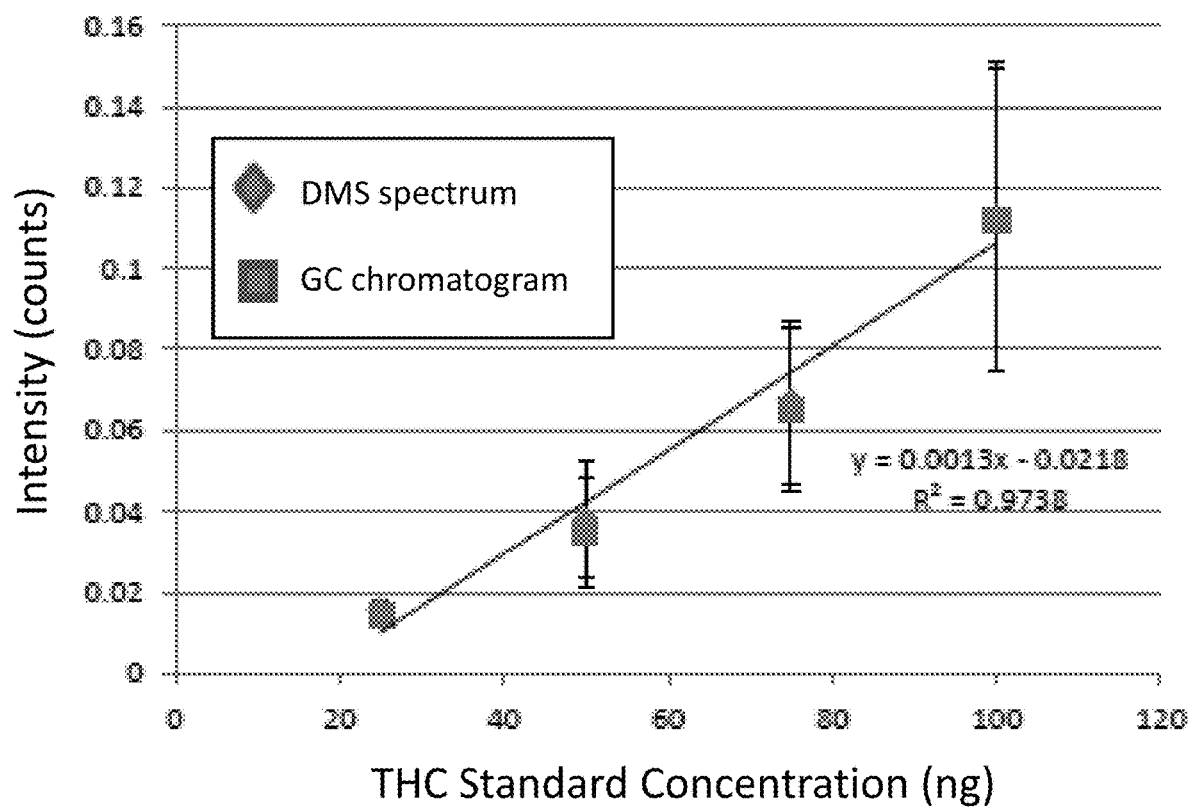
FIG. 11 is a graph of intensity as a function of THC standard concentration that illustrates representative IH-GC-DMS calibration curves for the DMS spectrum (diamonds) and GC chromatogram (squares) for a THC standard ranging in concentration from 25 ng to 100 ng.

The IH-GC-DMS response was tested with THC standard by directly loading it onto the particle-trapping component, which was then heated by IH and introduced into the GC-DMS for analysis. The IH-GC-DMS showed a more sensitive dynamic range of 10 ng to 100 ng, with a larger linear range of 25 ng to 100 ng. The limit of detection for THC standard in the IH-GC-DMS was 10 ng. The THC standard peak was detected at a $V_c$ of 1.25±0.20 V in the DMS spectrum with the $V_d$ at 700V. In the GC chromatogram THC standard had a retention time of 53±7 seconds. THC standard exhibited a linear response on the IH-GC-DMS in both the DMS spectrum and the GC chromatogram. FIG. 11 shows the linear calibration curve for both the DMS spectrum (diamonds) and the GC chromatogram (squares). These data have a linear fit with a slope of 0.0013 and an $R^2$ value of 0.9738. Due to the linear calibration curve the IH-GC-DMS has the potential to be used for both qualitative and quantitative detection of THC.

When non-inhalation human breath was captured on the particle-trapping components then doped with THC standard and analyzed by IH-GC-DMS, the THC standard displayed a reproducible response over days and with different non-inhalation breath volunteers. The baseline noise response for the IH-GC-DMS was at an intensity of 0.5 V. The non-inhalation human breath sample only produced a small peak at a $V_c$ of 3 V with an intensity of 0.6 V at a $V_d$ of 700 V. When 50 ng of THC standard was applied to a particle-trapping component, that already had non-inhalation breath collected onto the same particle-trapping component by the breath collector, there was a large THC standard peak detected at a $V_c$ of 1.25±0.20 V and an average intensity of 0.9 V. This THC standard with non-inhalation human breath response was reproducible over days, with different non-inhalation human breath samples, different breath collectors, and different particle-trapping components. The IH-GC-DMS also demonstrated a higher sensitivity to THC standard and minimal interferences with non-inhalation human breath due to the removal of the DMS membrane, and the addition of inductive heating desorption and the GC in front of the DMS.

The field studies were conducted by collecting samples from volunteers before and after they smoked cannabis in their private residences. After the samples were collected the particle-trapping components were taken back to the laboratory for analysis. A sample set was composed of a pre-inhalation breath sample and a post-inhalation breath sample collected from the same volunteer.

Figure 12:
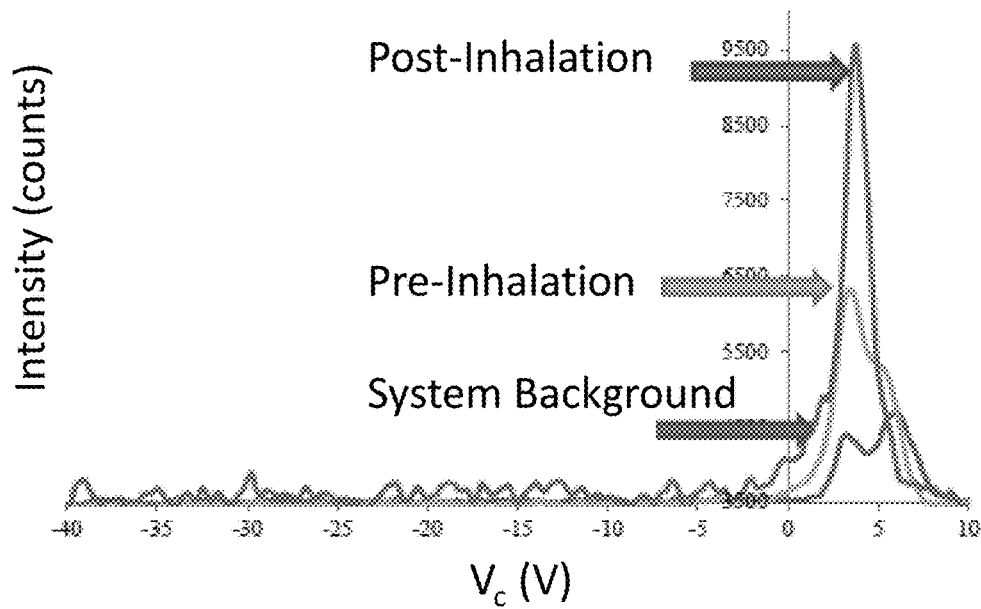
FIG. 12 is a combined IH-DMS spectrum illustrating spectra obtained from analysis of particle samples obtained from subjects' breath samples before ("pre-inhaled") and after ("post-inhalation") cannabis was inhaled, along with a system background sample ("system background").

Six sample sets were analyzed by the IH-DMS for the positive detection of THC from post-inhalation cannabis breath. The IH-DMS spectra were all taken at a $V_d$ of 1000 V. The plots displayed a full $V_c$ scan from −40 V to +10 V on the x-axis and intensity (counts) on the y-axis. FIG. 12 shows a true positive detection of THC from the post-inhalation breath. In a true positive spectrum the THC peak was easily detectable from the system background and the pre-inhalation sample; there was no possibility of misidentification. This demonstration is seen in the 3500 V intensity difference between the pre-inhalation and post-inhalation sample allowing the large post-inhalation peak at a $V_c$ of 3.75±0.18 V to be positively identified as THC. The THC $V_c$ value at the specific $V_d$ for the post-inhalation cannabis sample was also compared to the THC standard $V_c$ value at the specific $V_d$ for conformation of identification. A false negative was documented when either no THC was detected at a $V_c$ of 3.75±0.18 V and a $V_d$ of 1000 V or the pre-inhalation peak was larger than the post-inhalation peak.

For field deployed instruments it is common to set a level of detection stating anything above that level is a true positive and anything below that level is a true negative. There was a 33% true positive detection rate and a 67% false negative rate for THC from post-inhalation cannabis human breath samples. Out of the six sample sets only two of them showed a difference between pre-inhalation and post-inhalation breath. In the false negative spectra either there was no THC peak detected at a $V_c$ of 3.75±0.18 V and a $V_d$ of 1000 V or a larger peak was detected in the pre-inhalation breath at the same $V_c$ range at that specific $V_d$ as THC. If the peak in the pre-inhalation sample was THC then the intensity should have increased after inhaling; in fact the intensities decreased after inhaling so THC did not cause the large intensity pre-inhalation peak. The true negative rate was 83%; most of the pre-inhalation samples were under an intensity of 0.6. THC was detected in one of the pre-inhalation samples, making the actual false positive rate 17%. In some embodiments, IH-DMS methods exhibited less sensitivity; however, there were only a few interferences detected in the system and therefore it could be concluded that there was a very low false positive rate.

Figure 13:
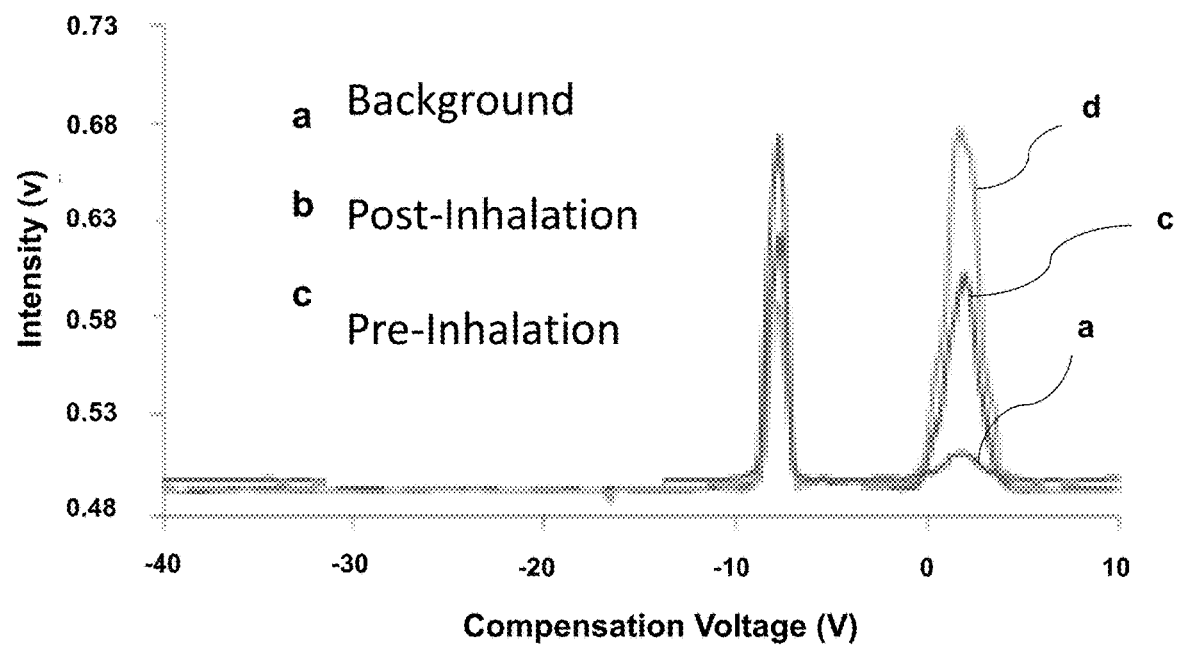
FIG. 13 is a combined IH-DMS spectrum illustrating a true positive response of detected THC in a subject after inhaling cannabis ("post-inhalation"); a pre-inhalation sample and background sample are included as comparisons.
Figure 14:
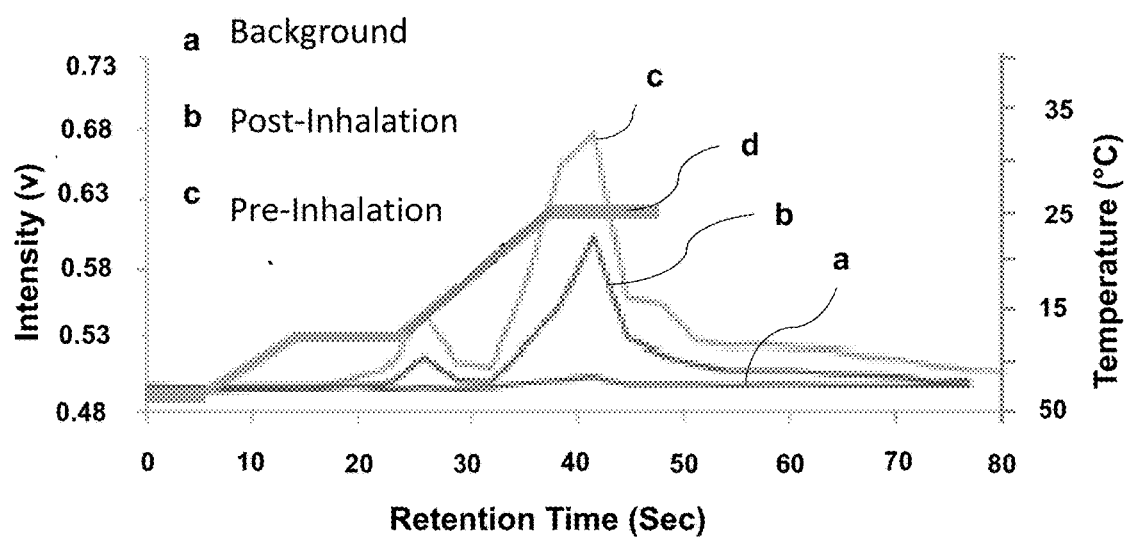
FIG. 14 is a chromatogram obtained from using gas chromatography to detect a true positive response of detected THC in a subject after inhaling cannabis ("post-inhalation"); a pre-inhalation sample and background sample are included as comparisons, along with a temperature ramp.

Nineteen sample sets of human breath, pre-inhalation and post-inhalation cannabis, were analyzed by the IH-GC-DMS. Each sample produced a DMS spectrum and a GC chromatogram; both forms of evidence were used to confirm the detection of THC from the samples. As seen in FIG. 13, the DMS spectra were recorded at a $V_d$ of 700 V and were displayed with the $V_c$ from −40 V to +10 V on the x-axis and intensity (V) on the y-axis. The GC chromatograms displayed retention time (s) on the x-axis and intensity (V) along with temperature (° C.) on the y-axis (FIG. 14). True positive results can be seen in FIG. 14, which shows an example of a true positive response for volunteer 24 in DMS spectra and a GC chromatogram. The THC peak in the DMS spectra was detected at a $V_d$ of 700 V by a decrease in the reactant ion peak at a $V_c$ of −8 V and an increase in intensity of the peak at a $V_c$ of 1.63±0.20 V. In the GC chromatogram two sets of peaks were detected in the pre-inhalation and post-inhalation breath. One set was at a retention time of ~25 seconds and the other set was at 43±6 seconds. The temperature of the column was only at 120° C. when the first set of peaks appeared at ~25 seconds. THC is not volatile at this low temperature, so the peak detected at a retention time of ~35 seconds was caused by more volatile contaminates from the breath sample. The THC peak was seen when the GC column reached 250° C. at the retention time of about 43±6 seconds. This identification was confirmed by comparing the retention times and $V_c$ with the THC standard. The THC standard had a retention time of 53±7 seconds and a $V_c$ of 1.25±0.20 V at a $V_d$ of 700 V, which is comparable to the THC seen in breath at a retention time of 43±6 seconds and a $V_c$ of 1.63±0.20 V at a $V_d$ of 700 V.

A false positive was documented when there was either no response at a retention time of 43±6 seconds and a $V_c$ of 1.63±0.20 V at a $V_d$ of 700 V or the pre-inhalation breath had a higher intensity peak than the post-inhalation breath at the same $V_c$ at a specific $V_d$ and retention time as THC. If the high intensity peak in the pre-inhalation breath sample was THC, then the intensity of the peak detected in the pre-inhalation breath should have increased after inhaling cannabis. This outcome did not occur; instead a decrease was seen in the post-inhalation breath peak intensity, hence indicating a false positive response.

In this embodiment, the true positive rate was 89% and false negative rate was 11%, the great majority of the post-inhalation samples gave a positive THC response demonstrating that this system was quite sensitive to THC. However, the true negative rate was 58% while the false positive rate was 42% in pre-inhalation samples; almost half the pre-inhalation breath samples gave a false THC response. Clearly, the IH-GC-DMS had a high detection rate for THC but there were numerous interferences that caused a high false positive rate.

The post-inhalation sample results for both the IH-DMS (white cells) and IH-GC-DMS (grey cells) are listed in Table 7. The table lists the volunteer's number, the date on which the sample was collected/analyzed, the instrument on which it was analyzed, whether the subjects ate or drank during the study, and if a positive THC response was detected. There were no trends found in the information on Table 7 between the two breath samples with the positive THC detection by the IH-DMS. The breath samples that contained the positive THC detection were on different days with different volunteers under different conditions (one volunteer drank during the study the other did not). The IH-GC-DMS analyzed 19 post-inhalation breath samples. No trends were found between the IH-GC-DMS false negative responses from the information listed on Table 7. The false negative responses were from different volunteers over a range of dates and inhalation devices. Only one volunteer, #3, on Jan. 31, 2016 drank mint water during the sample collection. This could have diluted the amount of THC on skin particles in their mouth at the time causing the false negative detection.

TABLE 7

| Vol. # | System analyzed | How they smoked | Drinking before sampling | Eating before sampling | THC Response |
|---|---|---|---|---|---|
| 16 | IH-DMS | Pipe | No | No | Yes |
| 17 | IH-DMS | Joint | No | Yes (Before any sampling) | No |
| 20 | IH-DMS | Pipe | No | No | No |
| 22 | IH-DMS | Bong | Yes (in-between inhaling and sampling) | No | Yes |
| 23 | IH-DMS | Joint | No | No | No |
| 19 | IH-DMS | Bong | No | No | No |
| 15 | IH-GC-DMS | Blunt | Yes (in-between inhaling and sampling) | No | Yes |
| 3 | IH-GC-DMS | Pipe | No | No | Yes |

TABLE 7-continued

| Vol. # | System analyzed | How they smoked | Drinking before sampling | Eating before sampling | THC Response |
|---|---|---|---|---|---|
| 18 | IH-GC-DMS | Bong | No | No | Yes |
| 19 | IH-GC-DMS | Bong | No | No | Yes |
| 21 | IH-GC-DMS | Bong | No | No | No |
| 18 | IH-GC-DMS | Bong | No | No | No |
| 24 | IH-GC-DMS | Bong | No | No | Yes |
| 25 | IH-GC-DMS | Bong | No | No | Yes |
| 14 | IH-GC-DMS | Bong | No | No | No |
| 26 | IH-GC-DMS | Bong | No | No | Yes |
| 27 | IH-GC-DMS | Bong | No | No | Yes |
| 28 | IH-GC-DMS | Bong | No | No | No |
| 29 | IH-GC-DMS | Pipe | No | No | Yes |
| 30 | IH-GC-DMS | Bong | No | No | Yes |
| 31 | IH-GC-DMS | Pipe | No | No | Yes |
| 33 | IH-GC-DMS | Bong | No | No | No |
| 3 | IH-GC-DMS | Pipe | Yes | No | No |
| 16 | IH-GC-DMS | Blunt | No | No | Yes |
| 32 | IH-GC-DMS | Pipe | No | No | Yes |

Both the IH-DMS and the IH-GC-DMS could detect THC standard when directly applied to the particle-trapping component. The detection of a THC standard when directly applied on a particle-trapping component with non-inhalation human breath was reproducible over days with different non-inhalation breath. The removal of the membrane on the DMS along with the addition of the inductive heater improved the sensitivity of the system to the THC standard. The GC in front of the DMS allowed for THC to be identified by a retention time of 43±6 seconds and a $V_c$ of 1.63±0.20 V at a $V_d$ of 700 V.

Both the IH-DMS and IH-GC-DMS can detect THC from post cannabis smoker's breath. The IH-DMS was not as sensitive to THC detection from post-inhalation breath, but also did not detect many interferences and as a consequence had a low false positive rate. The IH-GC-DMS had a detection rate of 89%, demonstrating that the system was very sensitive to THC detection from post-inhalation breath. The high false positive rate meant that there were many interferences also detected at the same retention time of 43±6 seconds and a $V_c$ of 1.63±0.20 V at a $V_d$ of 700 V that THC was detected.

The THC standards were more reproducible on the IH-DMS and IH-GC-DMS than THC detected from post-inhalation cannabis breath. The THC standard was directly applied to the particle-trapping component the amount of THC captured on the particle trap directly correlates with the collection time and the amount of THC adsorbed on the cannabis smoker's skin particles. Therefore an inconsistent THC response from the post-inhalation cannabis breath samples could indicate the collection time was not long enough or that THC was not adsorbed efficiently onto the skin particles.

The lower true positive detection rate for the IH-DMS was due to interferences in sample breath of pre-smokers. To separate these interferences, a GC must be added between the collector and the DMS detector. The GC is used to separate the THC from the interfering compounds. In addition, the GC is used to concentrate the THC at the head of the column.

Without the GC there might be some loss of THC vapor during the inductive heating process resulting in the fact that not all the THC was analyzed at once by the DMS; this could cause a decrease in signal. Similar to the GC acting as a trap, the carrier gas could likewise act as a trap. If the carrier gas was turned off during the inductive heating on the DMS there would be little loss of THC sample. After the THC is in the vapor state the carrier gas could be turned on resulting in the transferring of the THC vapor at once to the DMS for analysis. Control of the carrier gas on the IH-DMS would improve the THC concentration, in turn increasing the detection rate.

Improvements can still be made to the GC column temperature ramp to separate THC from contaminants with similar $V_c$-$V_d$ responses. Temperature ramping the inductive heater could provide another level of separation of contaminants from THC. The removal of the membrane from the DMS overall improved the detection of THC. Overall, however, the resulted obtained here are very encouraging toward the development of a breathalyzer based on DMS technology. A prototype with improved sensitivity, selectivity, and accuracy for the detection of THC from post-inhalation breath samples should be tested in real drugged driving roadside scenarios.

To decrease the power to reach the +200° C. temperatures required to volatilize THC, the 500 W thermal desorber was replaced by a 5 W inductive heating process. Inductive heating (IH) entails a direct rapid heating method powered by a 9 V battery which is capable of achieving temperatures up to 300° C. in a polymer coated steel wool particle trapping agent. THC standard applied to a particle trap was inductively heated and analyzed by either the DMS or the gas chromatography (GC)-DMS. The IH-DMS and IH-GC-DMS were able to detect THC down to 10 ng concentration levels.

The sensitivity of the DMS was increased by removal of the membrane located in front of the DMS cell. The membrane was originally used to decrease the number of contaminants and any moisture introduced into the sensor chip for analysis. The removal of the membrane in the DMS, along with the addition of the inductive heater process, improved the sensitivity of detection of the THC standard and THC collected from cannabis smokers' breath samples. The thermal desorber-DMS with the membrane used an average THC standard concentration of 100 µg, but with the inductive heater and the membrane removed from the DMS the average THC standard concentration used was decreased to 50 ng. The limit of detection for THC standard with the IH-DMS was 10 ng. The membrane removal did not increase the number of interferences detected with the IH-DMS; a low rate of false positive results was achieved with the post-inhalation cannabis field samples. The membrane removal did increase the number of false negatives detected; this system was indeed more sensitive to THC, but the selectivity did not improve.

A GC column was interfaced after the inductive heater and in front of the membrane-less DMS to increase the selectivity of the sample before analysis. The temperature program of the GC column caused the GC to act like a trap, allowing more volatile compounds to elute off of the column first before increasing the temperature to elute THC. The limit of detection for the IH-GC-DMS was 5 ng of THC standard. The selectivity of the IH-GC-DMS was tested with post cannabis smokers' breath samples for the detection of THC. The IH-GC-DMS had a detection rate of 89% for THC from post cannabis smokers' breath. This experiment demonstrated that the modified system featuring the inductive heater, the GC column, and the membrane removed was very selective to THC detection from post-inhalation breath.

Example 5

In this example, swabs were used to isolate saliva samples from subjects. Saliva samples also were collected by having the subject spit into a collection vial. The swab sample was obtained by swabbing a subject's cheek area, bottom gums, and/or tongue after a subject had inhaled cannabis. In some control embodiments, control swabs that were spiked with 8 ng of a THC standard were exposed to thermal desorption to determine how much THC can be extracted from the swab samples. In some embodiments, approximately 73% of the THC was obtained from the swab sample. In additional embodiments, approximately 86% was obtained. In some embodiments, saliva samples can be analyzed by utilizing an extraction technique to isolate THC from the saliva sample by using the following steps: oral fluid is collected in a vial (2 mL) and transferred 1 mL to another vial by pipette; 100 uL of saliva is extracted by 400 uL of methanol or acetonitrile; the sample is vortexed for 30 seconds, centrifuged for 5 minutes at 13,000 rpm; and 185 uL of supernatant is spiked with 15 uL of THC-D3 for HPLC-MS analysis.

Figure 15:
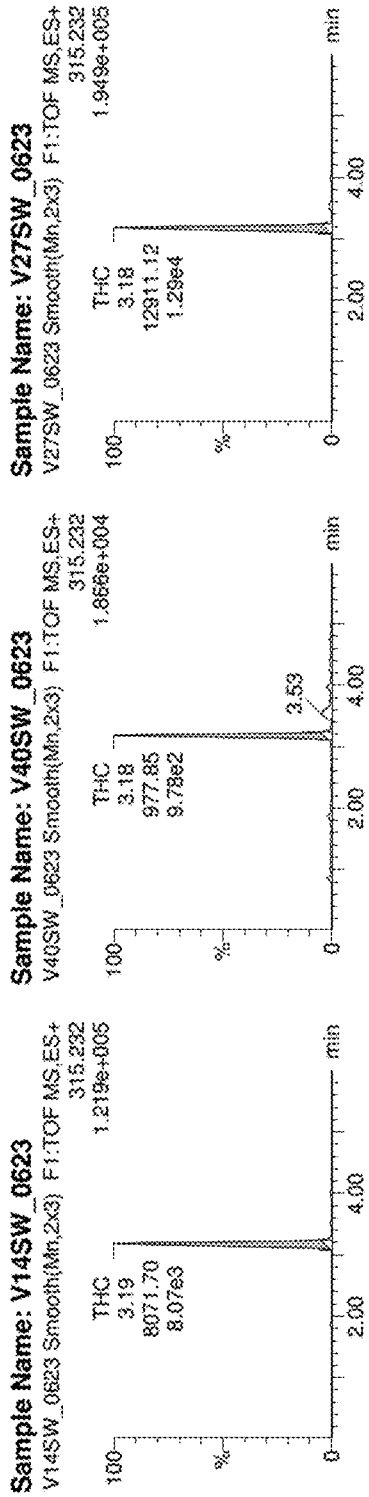
FIG. 15 includes exemplary mass spectra showing results from analyzing swab samples.

Exemplary results obtained from using an exemplary method with a mass spectrometry technique are illustrated in FIG. 15. Results also are tabulated in Table 8, below.

TABLE 8

| Volunteer | THC on Swab (ng) | THC in Spit (ng) |
| --- | --- | --- |
| V14 | 380.75 | 2110.1 |
| V27 | 673.5 | 2259.2 |
| V40 | 45.5 | 129.6 |

Example 6

In this example, the ability of method and device embodiments disclosed herein to detect the presence of an analyte in a sample and simultaneously render any potential DNA in the sample undetectable without destroying the integrity of analytes present in the sample was evaluated. In this example, synthetic saliva samples were evaluated, known quantities of DNA were used, and direct measurements of remaining DNA in a forensic sample following treatment were conducted. Detection of residual DNA was performed using the polymerase chain reaction (PCR) for quantitation of any remaining genetic material.

A control sample comprising only synthetic saliva, to ensure no DNA was present, was used. Approximately 7 ng/uL of DNA was added to each sample used to examine destruction of genetic material. Using variations of controls, destruction treatments, and different concentrations of DNA the following sample types were constructed.

Type 1—Control sample with only synthetic saliva (no DNA)
Type 2—Synthetic saliva containing 7 ng/uL of DNA was boiled followed by PCR analysis. The purpose of this sample was used to establish the baseline levels of DNA found. A second sample was boiled for 10 minutes to allow the DNA to be expressed. This sample was used to establish a baseline for the amount of DNA present in a saliva sample.

Type 3—Synthetic saliva with a known quantity of DNA (7 ng/uL) was placed onto a chemical extraction/capture cartridge commonly used for breath/oral fluid capture of drugs of abuse (but may be used for capture of other materials too) and extracted using the following procedure: the sample was placed inside a microcentrifuge tube and suitable amount of (e.g., 600 pL) of 50 mM NaOH was added. The tube containing the sample was closed and then vortexed for 10 minutes. The tube was then heated at 95° C. for 10 min. Finally, 120 pL 1 M Tris (pH 8.0) was added to the tube. The resulting sample solution containing genomic DNA was stored at 4° C. This sample type was used to establish the baseline for how much genetic material is lost during the extraction process from an analyte collection device.

Type 4—The fourth sample type was an extension of Type 3 but subjected to rapid inductive heating for 10 seconds in a device embodiment according to the present disclosure, which enables heating at temperature ranges disclosed herein, such as at a temperature of 250° C. Following this rapid heating step, the sample cartridge containing the sample was subjected to the sample DNA extraction process outlined for Type 3 samples. Reduction in the levels of extractable/usable DNA are reflected in an increase in the number of PCR cycles necessary to observe sufficient levels of DNA. Using the Bio Rad PCR instrument, if more than 38-40 cycles of replication are initiated without exceeding the threshold for detection, no usable genetic material is present.

Type 5—The fifth sample type is a variant of Type 4 which is subjected to an additional 60 seconds of inductive heating. This sample type was also subjected to the DNA extraction and replication procedure to evaluate the impact of extended firing times.

Type 6—The sixth sample type further extended the conditions of Type 4 with an additional 120 seconds inductive firing time. This sample type was also subjected to the DNA extraction and replication procedure to evaluate the impact of extended firing times.

Figure 17:
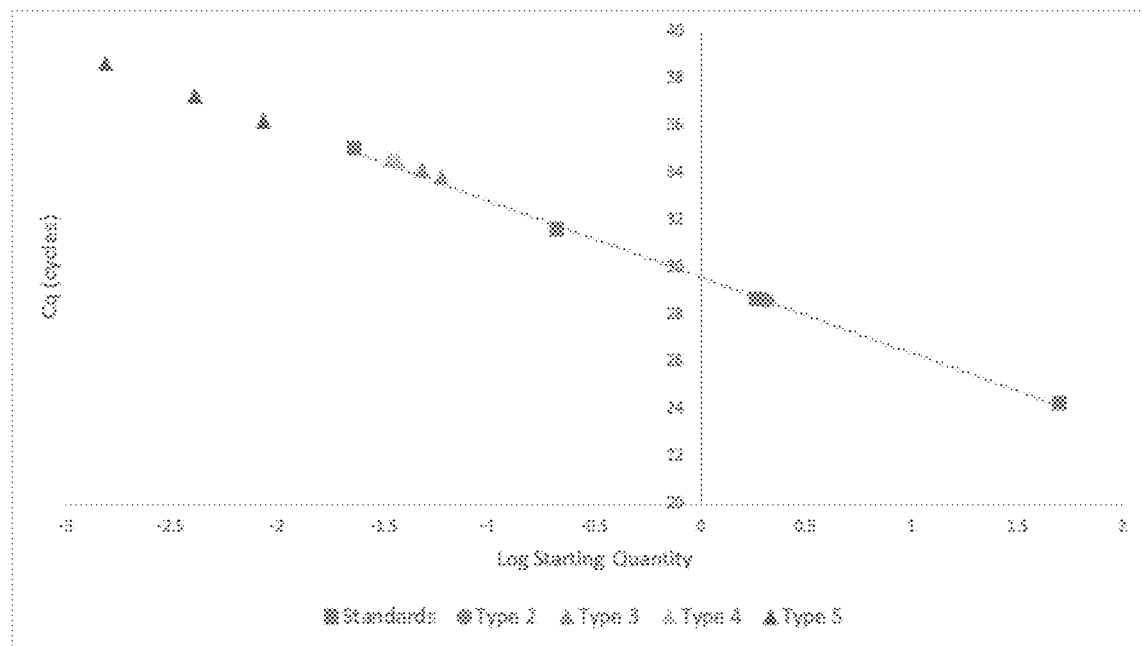
FIG. 17 is a graph showing the number of PCR cycles used to observe meaningful levels of DNA amplification compared to initial starting concentrations of DNA in samples exposed to method and device embodiments described herein.
Figure 18:
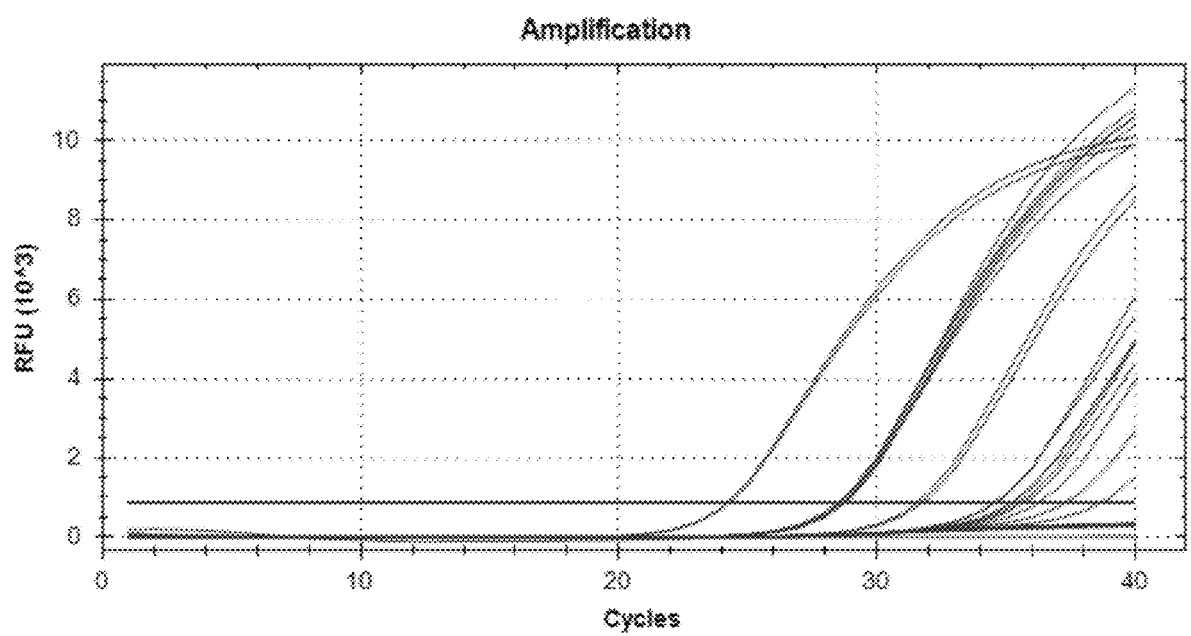
FIG. 18 is a graph of raw data showing when amplified DNA begins to exhibit fluorescence thereby indicating that DNA is present in the sample.

PCR Results—To assess the levels of DNA present all sample types were probed using the manufacturer's instructions found in Quantifiler® Human DNA Quantification Kit (Applied Biosystems). Individual sample types were examined in the context of a set of DNA standards with known quantities of DNA ranging from 0.023 ng/uL to 50.0 ng/uL. FIG. 17 illustrates the number of PCR (Cq) used to realize meaningful levels of DNA amplification compared to the initial starting concentrations. Solid squares represent the samples containing known quantities of DNA, whereas, the triangle markers correspond to the sample types containing DNA deposited onto the sampling medium with and without inductive heating. FIG. 18 provides raw data showing when amplified DNA begins to fluoresce, meaning DNA was present. DNA is counted as present at the cycle where the line crosses the $1 \times 10^3$ RFU threshold. The y-axis is in relative fluorescence units, the x-axis the number of PCR cycles conducted. Table 9, below, shows DNA quantification results for all sample types discussed above and further illustrates that after 120 seconds of firing in some embodiments, no DNA is present on the sampling medium.

TABLE 9

| Sample Type | Contents | Lab Procedure | CQ (cycles) | CQ Mean | CQ StDev | DNA (ng/uL) | Mean DNA (ng/uL) | StDev DNA (ng/uL) |
|---|---|---|---|---|---|---|---|---|
| I | Saliva | None | ND<br>ND | ND<br>ND | ND<br>ND | ND<br>ND | ND<br>ND | ND<br>ND |
| II | Saliva + DNA | Boiled for 10 minutes | 28.58<br>28.59 | 0.01 | 0.01 | 2.0513<br>2.0731 | 2.0622 | 0.0154 |
| III | Saliva + DNA | Extracted | 33.82<br>34.13 | 0.22 | 0.22 | 0.0598<br>0.0481 | 0.0540 | 0.0083 |
| IV | Saliva + DNA | Triton Fired + Extraction | 34.60<br>34.49 | 0.08 | 0.08 | 0.0343<br>0.0371 | 0.0357 | 0.0019 |
| V | Saliva + DNA | Triton Fired + 60 s extra firing + Extraction | 36.23<br>37.28<br>38.66<br>ND | 1.22 | 1.22 | 0.0086<br>0.0041<br>0.0015<br>ND | 0.0047 | 0.0036 |
| VI | Saliva + DNA | Triton Fired + 120 s extra firing + Extraction | ND<br>ND<br>ND<br>ND | ND<br>ND<br>ND<br>ND | ND<br>ND<br>ND<br>ND | ND<br>ND<br>ND<br>ND | ND<br>ND<br>ND<br>ND | ND<br>ND<br>ND<br>ND |

In view of the many possible embodiments to which the principles of the present disclosure may be applied, it should be recognized that the illustrated embodiments are only preferred examples and should not be taken as limiting the scope of the claimed invention. Rather, the scope is defined by the following claims. We therefore claim as our invention all that comes within the scope and spirit of these claims.

We claim:

1. A method, comprising:
   exposing a saliva and/or mucous particle sample obtained from a subject to heat using thermal desorption to produce a volatilized sample from a solid component of the saliva and/or mucous particle sample, wherein the solid component is a skin particle and/or a hair particle onto which $\Delta^9$-tetrahydrocannabinol (THC) is absorbed; and analyzing the volatilized sample to determine a presence of the THC absorbed onto the solid component of the saliva and/or mucous particle sample prior to thermal desorption using spectrometry detection techniques, visual detection techniques, chromatography detection techniques, or combinations thereof.

2. The method of claim 1, wherein the saliva and/or mucous particle sample is obtained from the subject's mouth, tongue, or nose.

3. The method of claim 1, wherein exposing the saliva and/or mucous particle sample to heat comprises exposing the saliva and/or mucous particle sample to a heat source.

4. The method of claim 3, wherein the heat source is maintained at temperatures ranging from 100° C. to 500° C. so as to render any nucleic acid components present in the solid skin particle and/or the hair particle of the saliva and/or mucous particle sample undetectable by a detection technique.

5. The method of claim 1, wherein the thermal desorption comprises heating a surface in contact with the saliva and/or mucous particle sample so as to increase the surface's temperature.

6. The method of claim 1, wherein the thermal desorption comprises using inductive heating.

7. The method of claim 1, wherein analyzing the volatilized sample comprises using a spectrometry detection technique, a chromatography detection technique, or a combination thereof, whereby the presence of THC, other drugs, or metabolites thereof, is confirmed by a presence of a signature peak.

8. The method of claim 7, wherein the spectrometry detection technique is ion mobility spectrometry and the signature peak has a reduced mobility value ($K_0$) of 1.07 $cm^2V^{-1}s^{-1}$.

9. The method of claim 1, wherein the spectrometry detection technique is selected from differential mobility spectrometry, ion mobility spectrometry, photospectrometry, mass spectrometry, or a combination thereof; and the chromatography detection technique is selected from gas chromatography, liquid chromatography, or a combination thereof.

10. The method of claim 1, wherein analyzing the volatilized sample comprises using a visual detection technique whereby the presence of THC, other drugs, or metabolites thereof, is confirmed by visualizing a color change by naked eye or by using ultraviolet-visible (UV/Vis) spectroscopy.

11. The method of claim 1, wherein the method further comprises obtaining the saliva and/or mucous particle sample from the subject.

12. A method, comprising:
obtaining a particle sample from a subject by isolating breath comprising the particle sample from the subject and directing the particle sample into a first device comprising, (i) a particle-trapping component comprising a collecting medium configured to trap the particle sample introduced into the device; and (ii) a heat source detachably coupled to the particle-trapping component and further configured to expose the particle sample introduced into the first device to a temperature ranging from 100° C. to 500° C.; and wherein the particle sample comprises a solid skin particle and/or a hair particle;
exposing the particle sample to the heat source of the first device to produce a volatilized sample from the solid skin particle and/or hair particle of the particle sample; and
analyzing the volatilized sample with a detection device detachably coupled to the first device to determine a presence of $\Delta^9$-tetrahydrocannabinol (THC) in the particle sample by viewing a THC signature peak, a color change, or a read-out message if THC is present.

13. The method of claim 12, wherein the first device further comprises:
a detachable sample conduit;
a body configured to receive the particle-trapping component, wherein the body is detachably coupled to the detachable sample conduit; and
a collecting medium disposed within the particle-trapping component, wherein the collecting medium is configured to trap the particle sample introduced into the sample conduit.

14. A method, comprising:
obtaining a particle sample from a subject by isolating breath comprising the particle sample from the subject and collecting the particle sample from the subject wherein the particle sample comprises a solid skin particle and/or hair particle;
directing the particle sample into a first device, comprising (i) a particle-trapping component comprising a collecting medium configured to trap the particle sample introduced into the device; and (ii) a heat source detachably coupled to the particle-trapping component and further configured to expose the particle sample introduced into the first device to a temperature ranging from 100° C. to 500° C., such that the particle sample is introduced into the particle-trapping component;
exposing the particle sample to heat using thermal desorption to produce a volatilized sample from the solid skin particle and/or hair particle of the particle sample; and
analyzing the volatilized sample with a detection device detachably coupled to the first device to determine a presence of one or more signature peaks and/or color changes, or a corresponding read-out representing a signature peak and/or color change, provided by the detection device, wherein the one or more signature peaks and/or color changes, or the corresponding read-out, indicates a presence of $\Delta^9$-tetrahydrocannabinol (THC), other drugs, or metabolites thereof in the particle sample.

15. The method of claim 14, wherein the particle sample is obtained from the subject's mouth, tongue, or nose.

16. The method of claim 14, wherein obtaining the particle sample comprises dislodging the particle sample from the subject by pulsating air or liquid into the subject's mouth or nose or onto the subject's tongue.

17. The method of claim 14, wherein the first device further comprises:
a detachable sample conduit;
a body configured to receive the particle-trapping component, wherein the body is detachably coupled to the detachable sample conduit; and
a collecting medium disposed within the particle-trapping component, wherein the collecting medium is configured to trap the particle sample introduced into the sample conduit.

* * * * *